United States Patent
Corrie et al.

(10) Patent No.: US 9,387,000 B2
(45) Date of Patent: Jul. 12, 2016

(54) ANALYTE DETECTION USING A NEEDLE PROJECTION PATCH

(75) Inventors: Simon Robert Corrie, New Farm (AU); Mark Anthony Fernance Kendall, Chelmer (AU)

(73) Assignee: The University of Queensland, St. Lucia (AU)

( * ) Notice: Subject to any disclaimer, the term of this patent is extended or adjusted under 35 U.S.C. 154(b) by 494 days.

(21) Appl. No.: 12/992,593

(22) PCT Filed: May 22, 2009

(86) PCT No.: PCT/AU2009/000637
§ 371 (c)(1),
(2), (4) Date: Feb. 16, 2011

(87) PCT Pub. No.: WO2009/140735
PCT Pub. Date: Nov. 26, 2009

(65) Prior Publication Data
US 2011/0160069 A1    Jun. 30, 2011

(30) Foreign Application Priority Data

May 23, 2008    (AU) .............................. 2008902578

(51) Int. Cl.
G01N 33/53        (2006.01)
A61B 17/20        (2006.01)
G01N 33/543       (2006.01)

(52) U.S. Cl.
CPC ........ *A61B 17/205* (2013.01); *G01N 33/54366* (2013.01); *B01J 2219/00504* (2013.01); *B01J 2219/00509* (2013.01); *B01J 2219/00527* (2013.01); *B01J 2219/00605* (2013.01); *B01J 2219/00621* (2013.01); *B01J 2219/00637* (2013.01)

(58) Field of Classification Search
CPC .................................................... C40B 30/00
USPC ............................................................. 506/7
See application file for complete search history.

(56) References Cited

U.S. PATENT DOCUMENTS

| | | |
|---|---|---|
| 2,881,500 A | 4/1959 | Furness |
| 4,702,799 A | 10/1987 | Tuot |
| 5,201,992 A | 4/1993 | Marcus et al. |
| 5,353,792 A | 10/1994 | Lübbers et al. |
| 5,449,064 A | 9/1995 | Hogan et al. |
| 5,457,041 A | 10/1995 | Ginaven et al. |
| 5,499,474 A | 3/1996 | Knooihuizen |
| 5,527,288 A | 6/1996 | Gross et al. |
| 5,611,806 A | 3/1997 | Jang |
| 5,859,937 A | 1/1999 | Nomura |
| 5,922,356 A | 7/1999 | Koseki et al. |
| 5,928,207 A | 7/1999 | Pisano et al. |
| 6,052,652 A | 4/2000 | Lee |
| 6,287,556 B1 | 9/2001 | Portnoy et al. |
| 6,299,621 B1 | 10/2001 | Fogarty et al. |
| 6,334,856 B1 | 1/2002 | Allen et al. |
| 6,352,697 B1 | 3/2002 | Cox et al. |
| 6,454,755 B1 | 9/2002 | Godshall |
| 6,463,312 B1 | 10/2002 | Bergveld et al. |
| 6,478,738 B1 | 11/2002 | Hirabayashi et al. |
| 6,503,231 B1 * | 1/2003 | Prausnitz et al. ............. 604/272 |
| 6,551,849 B1 * | 4/2003 | Kenney ........................... 438/34 |
| 6,557,849 B2 | 5/2003 | Wyss |
| 6,558,361 B1 * | 5/2003 | Yeshurun ..................... 604/272 |
| 6,589,202 B1 * | 7/2003 | Powell ............................ 604/27 |
| 6,591,124 B2 | 7/2003 | Sherman et al. |
| 6,743,211 B1 | 6/2004 | Prausnitz et al. |
| 6,749,575 B2 * | 6/2004 | Matriano et al. ............. 600/564 |
| 6,855,372 B2 | 2/2005 | Trautman et al. |
| 6,881,203 B2 | 4/2005 | Delmore et al. |
| 6,908,453 B2 | 6/2005 | Fleming et al. |
| 6,923,764 B2 | 8/2005 | Aceti et al. |
| 6,931,277 B1 * | 8/2005 | Yuzhakov et al. ............. 604/21 |
| 6,945,952 B2 | 9/2005 | Kwon |
| 7,022,071 B2 | 4/2006 | Schaupp et al. |
| 7,045,069 B2 * | 5/2006 | Ozeryansky ................... 216/11 |
| 7,097,631 B2 | 8/2006 | Trautman et al. |
| 7,169,600 B2 | 1/2007 | Hoss et al. |
| 7,211,062 B2 | 5/2007 | Kwon |
| 7,250,037 B2 | 7/2007 | Shermer et al. |
| 7,753,888 B2 * | 7/2010 | Mukerjee et al. ............. 604/173 |
| 8,052,633 B2 * | 11/2011 | Kendall .......................... 604/19 |
| 8,062,573 B2 * | 11/2011 | Kwon ........................... 264/319 |
| 8,734,697 B2 * | 5/2014 | Chen et al. ................... 264/219 |

(Continued)

FOREIGN PATENT DOCUMENTS

| | | |
|---|---|---|
| CN | 101214395 A | 7/2008 |
| CN | 101297989 A | 11/2008 |

(Continued)

OTHER PUBLICATIONS

Kendall (WO 2005/072630, "Device for Delivery of Bioactive Materials and Other Stimuli").*
Chinese Office Action mailed Feb. 17, 2012, for Chinese Patent Application No. 200980104635.3, 7 pages.
Aichele et al., "Antiviral Cytotoxic T Cell Response Induced by In Vivo Priming With a Free Synthetic Peptide," *Journal of Experimental Medicine* 171:1815-1820, May 1990.
Albert et al., "Dendritic cells acquire antigen from apoptotic cells and induce class I-restricted CTLs," *Nature* 392(6671):86-89, Mar. 1998.
Albert et al., "Tumor-specific killer cells in paraneoplastic cerebellar degeneration," *Nature Medicine* 4(11):1321-1324, Nov. 1998.
Anderson, "Cutaneous Microdialysis: Is it Worth the Sweat?," *Journal of Investigative Dermatology* 126:1207-1209, 2006.
Athanasopoulos et al., "Gene therapy vectors based on adeno-associated virus: characteristics and applications to acquired and inherited diseases (Review)," *International Journal of Molecular Medicine* 6(4):363-375, 2000.
Bachmann et al., "Dendritic cells process exogenous viral proteins and virus-like particles for class I presentation to CD8+cytotoxic T lymphocytes," *European Journal of Immunology* 26(11):2595-2600, 1996.

(Continued)

*Primary Examiner* — Ann Lam
(74) *Attorney, Agent, or Firm* — Seed IP Law Group PLLC

(57) ABSTRACT

Apparatus for use in detecting analytes in a subject, wherein the apparatus includes a number of projections provided on a patch, such that applying the patch to the subject causes at least some of the projections to be inserted into the subject and target one or more analytes and a reagent for detecting the presence or absence of analytes.

42 Claims, 19 Drawing Sheets

(56) References Cited

U.S. PATENT DOCUMENTS

| | | |
|---|---|---|
| 8,883,015 B2 | 11/2014 | Kendall et al. |
| 2002/0008530 A1 | 1/2002 | Kim et al. |
| 2002/0016562 A1 | 2/2002 | Cormier et al. |
| 2002/0128599 A1 | 9/2002 | Cormier et al. |
| 2002/0177839 A1 | 11/2002 | Cormier et al. |
| 2003/0036710 A1 | 2/2003 | Matriano et al. |
| 2003/0199810 A1* | 10/2003 | Trautman et al. ............. 604/46 |
| 2004/0002121 A1* | 1/2004 | Regan et al. .................... 435/7.2 |
| 2004/0039397 A1 | 2/2004 | Weber et al. |
| 2005/0042866 A1 | 2/2005 | Klapproth et al. |
| 2005/0089553 A1* | 4/2005 | Cormier ............... A61K 9/0021 424/448 |
| 2005/0126710 A1 | 6/2005 | Laermer et al. |
| 2005/0137531 A1 | 6/2005 | Prausnitz et al. |
| 2005/0143713 A1 | 6/2005 | Delmore et al. |
| 2005/0197308 A1 | 9/2005 | Dalton et al. |
| 2005/0261632 A1 | 11/2005 | Xu ................................ 604/173 |
| 2006/0015061 A1 | 1/2006 | Kuo et al. |
| 2006/0055724 A1 | 3/2006 | Krawczyk et al. |
| 2006/0074376 A1 | 4/2006 | Kwon |
| 2006/0195125 A1 | 8/2006 | Sakakine et al. |
| 2006/0264782 A1 | 11/2006 | Holmes et al. |
| 2007/0027474 A1 | 2/2007 | Lasner |
| 2007/0060867 A1 | 3/2007 | Xu |
| 2007/0078376 A1 | 4/2007 | Smith |
| 2007/0224252 A1 | 9/2007 | Trautman et al. |
| 2007/0264749 A1 | 11/2007 | Birkmeyer |
| 2007/0270738 A1 | 11/2007 | Wu |
| 2007/0299388 A1 | 12/2007 | Chan et al. |
| 2008/0108959 A1 | 5/2008 | Jung et al. |
| 2008/0245764 A1 | 10/2008 | Pirk et al. |
| 2008/0312610 A1 | 12/2008 | Binks et al. |
| 2008/0312669 A1 | 12/2008 | Vries et al. |
| 2009/0017210 A1 | 1/2009 | Andrianov et al. |
| 2010/0221314 A1 | 9/2010 | Matsudo et al. |
| 2010/0222743 A1 | 9/2010 | Frederickson et al. |
| 2011/0028905 A1 | 2/2011 | Takada |
| 2011/0059150 A1 | 3/2011 | Kendall et al. |
| 2011/0223542 A1 | 9/2011 | Kendall |
| 2011/0245776 A1 | 10/2011 | Kendall |
| 2011/0288484 A1 | 11/2011 | Kendall et al. |
| 2012/0027810 A1 | 2/2012 | Chen et al. |
| 2012/0041412 A1* | 2/2012 | Roth .................... A61M 25/10 604/500 |
| 2012/0083741 A1* | 4/2012 | Kendall ....................... 604/173 |
| 2012/0083762 A1* | 4/2012 | Kendall ....................... 604/506 |
| 2012/0330250 A1 | 12/2012 | Kuwahara et al. |
| 2013/0190794 A1 | 7/2013 | Kendall et al. |
| 2014/0257188 A1 | 9/2014 | Kendall et al. |

FOREIGN PATENT DOCUMENTS

| | | |
|---|---|---|
| EP | 0 139 286 A2 | 5/1985 |
| EP | 1 695 734 B1 | 6/2008 |
| EP | 2 327 419 A1 | 6/2011 |
| JP | 2007-260889 A | 10/2007 |
| WO | 91/06571 A1 | 5/1991 |
| WO | 94/24281 A1 | 10/1994 |
| WO | WO 98/28037 A1 * | 7/1998 |
| WO | 99/02694 A1 | 1/1999 |
| WO | 99/42564 A2 | 8/1999 |
| WO | 99/64580 A1 | 12/1999 |
| WO | 00/05339 A1 | 2/2000 |
| WO | 00/42215 A1 | 7/2000 |
| WO | 00/74763 | 12/2000 |
| WO | 00/74764 A1 | 12/2000 |
| WO | 01/33614 A1 | 5/2001 |
| WO | 01/85207 A2 | 11/2001 |
| WO | 02/064193 A2 | 8/2002 |
| WO | 02/074173 A1 | 9/2002 |
| WO | 02/075794 A2 | 9/2002 |
| WO | 02/085446 A2 | 10/2002 |
| WO | 02/085447 A2 | 10/2002 |
| WO | 02/100476 A2 | 12/2002 |
| WO | 03/020359 A2 | 2/2003 |
| WO | 03/026732 | 4/2003 |
| WO | 03/048031 A2 | 6/2003 |
| WO | 03/053258 A1 | 7/2003 |
| WO | 03/092785 A1 | 11/2003 |
| WO | 04/000389 A2 | 12/2003 |
| WO | 2004/024224 A1 | 3/2004 |
| WO | 2005/049108 A2 | 6/2005 |
| WO | 2005/060621 A2 | 7/2005 |
| WO | 2005/069736 A2 | 8/2005 |
| WO | 2005/072630 A1 | 8/2005 |
| WO | 2005/123173 A1 | 12/2005 |
| WO | 2006/055799 A1 | 5/2006 |
| WO | 2006/101459 A1 | 9/2006 |
| WO | 2006/108185 A1 | 10/2006 |
| WO | 2006/116281 A2 | 11/2006 |
| WO | 2006/138719 A2 | 12/2006 |
| WO | 2007/002123 A2 | 1/2007 |
| WO | 2007/002521 A2 | 1/2007 |
| WO | 2007/012114 A1 | 2/2007 |
| WO | 2007/030477 A2 | 3/2007 |
| WO | 2007/054090 A1 | 5/2007 |
| WO | 2007/061781 A1 | 5/2007 |
| WO | 2007/070004 A2 | 6/2007 |
| WO | 2007/080427 A2 | 7/2007 |
| WO | 2007/127976 A2 | 11/2007 |
| WO | 2008/010681 A1 | 1/2008 |
| WO | 2008/011625 A2 | 1/2008 |
| WO | 2008/053481 A1 | 5/2008 |
| WO | 2008/069566 A1 | 6/2008 |
| WO | WO 2009040548 A1 * | 4/2009 |
| WO | 2009/066763 A1 | 5/2009 |
| WO | 2009/079712 A1 | 7/2009 |
| WO | 2009/081122 A1 | 7/2009 |
| WO | 2009/097660 A1 | 8/2009 |
| WO | 2009/140735 A1 | 11/2009 |
| WO | 2010/042996 A1 | 4/2010 |
| WO | 2010/071918 A1 | 7/2010 |
| WO | 2010/109471 A1 | 9/2010 |
| WO | 2011/105496 A1 | 9/2011 |
| WO | 2011/116388 A1 | 9/2011 |

OTHER PUBLICATIONS

Camilli et al., "*Listeria monocytogenes* Mutants Lacking Phosphatidylinositol-specific Phospholipase C are Avirulent," *Journal of Experimental Medicine* 173:751-754, Mar. 1991.

Cormier et al., "Transdermal delivery of desmopressin using a coated microneedle array patch system," *Journal of Controlled Release* 97(3):503-511, 2004.

Cox et al., "Adjuvants—a classification and review of their modes of action," *Vaccine* 15(3):248-256, 1997.

Dreyer, "Microneedles: Microprocessing in medicine," Final Presentation, ENMA465 Project, URL=http://www.mse.umd.edu/undergrad/courses/ENMA465-project-results.html, May 10, 2004, 23 pages.

Feng et al., "Molecular Biomarkers for Cancer Detection in Blood and Bodily Fluids," *Critical Reviews in Clinical Laboratory Sciences* 43(5-6):497-560, 2006.

Gao et al., "Priming of influenza virus-specific cytotoxic T lymphocytes vivo by short synthetic peptides," *Journal of Immunology* 147(10):3268-3273, Nov. 1991.

Gardeniers et al., "Silicon micromachined hollow microneedles for transdermal liquid transport," *Journal of Microelectromechanical Systems* 12(6):855-862, Dec. 2003.

Gill et al., "Coated microneedles for transdermal delivery," *Journal of Controlled Release* 117(2):227-237, 2007.

Gill et al., "Coating formulations for Microneedles," *Pharmaceutical Research* 24(7):1369-1380, Jul. 2007.

Ito et al., "Evaluation of self-dissolving needles containing low molecular weight heparin (LMWH) in rats," *International Journal of Pharmaceutics* 349(1-2):124-129, 2008.

Ito et al., "Feasibility of microneedles for percutaneous absorption of insulin," *European Journal of Pharmaceutical Sciences* 29(1):82-88, 2006.

Ito et al., "Self-dissolving microneedles for the percutaneous absorption of EPO in mice," *Journal of Drug Targeting* 14(5):255-261, 2006.

(56) References Cited

OTHER PUBLICATIONS

Jondal et al., "MHC Class I—Restricted CTL Responses to Exogenous Antigens," *Immunity* 5(4):295-302, Oct. 1996.
Kay et al., "Viral vectors for gene therapy: the art of turning infectious agents into vehicles of therapeutics," *Nature Medicine* 7(1):33-40, Jan. 2001.
Kendall et al., "The mechanical properties of the skin epidermis in relation to targeted gene and drug delivery," *Biomaterials* 28(33): 4968-4977, 2007.
Kuzu et al., "In vivo priming effect during various stages of ontogeny of an influenza A virus nucleoprotein peptide," *European Journal of Immunology* 23(6):1397-1400, 1993.
Kwon, "Acne Treatment by a Dissolvable Micro-Needle Patch," Controlled Release Society 33rd Annual Meeting, 2006, 2 pages.
Kwon, "In Vitro Evaluation of Transdermal Drug Delivery by a Micro-needle Patch," Abstract #115, Controlled Release Society 31st Annual Meeting TRANSACTIONS, 2004, 2 pages.
Kwon, "In Vitro Modeling of Transdermal PTH Delivery by Dissolving Micro-needle Patch," TheraJect Web Site (2007), 2 pages.
Kwon, "Rapid Intradermal Drug Delivery by a Dissolvable Micro-Needle Patch," Abstract #306, Controlled Release Society 32nd Annual Meeting & Exposition TRANSACTIONS, 2005, 2 pages.
Lee et al., "Dissolving microneedles for transdermal drug delivery," *Biomaterials* 29(13):2113-2124, 2008.
Lin et al., "Silicon-processed microneedles," *IEEE Journal of Microelectromechanical Systems* 8(1):78-79, Mar. 1999.
Matriano et al., "Macroflux® Microprojection Array Patch Technology: A New and Efficient Approach for Intracutaneous Immunization," *Pharmaceutical Research* 19(1):63-70, Jan. 2002.
Mengaud et al., "Expression in *Escherichia coli* and Sequence Analysis of the Listeriolysin O Determinant of *Listeria monocytogenes*," *Infection and Immunity* 56(4):766-772, Apr. 1988.
Miyano et al., "Hydrolytic Microneedles as Transdermal Drug Delivery System," *International Solid-State Sensors, Actuators and Microsystems Conference TRANSDUCERS 2007*, pp. 355-358, Jun. 10-14, 2007.
Miyano et al., "Sugar Micro Needles as Transdermic Drug Delivery System," *Biomedical Microdevices* 7(3):185-188, 2005.
Moore et al., "Introduction of soluble protein into the class I pathway of antigen processing and presentation," *Cell* 54(6):777-785, Sep. 9, 1988.
Mukerjee et al., "Microneedle array for transdermal biological fluid extraction and in situ analysis," *Sensors and Actuators A* 114:267-275, 2004.
Oh et al., "Demonstration of Dose-controlled Delivery by Dissolvable Micro-needle Arrays," Controlled Release Society 34th Annual Meeting and Exposition Jun./Jul. 7-11, 2007, 2 pages.
Oh et al., "Intradermal influenza vaccine delivery using skin-penetrating dissolvable vaccine microneedles," AAPS Annual Meeting and Exposition, 2006, 1 page.
Palmer et al., "Streptolysin O: a proposed model of allosteric interaction between a pore-forming protein and its target lipid bilayer," *Biochemistry* 37(8):2378-2383, Feb. 1998.
Park et al., "Biodegradable polymer microneedles: Fabrication, mechanics and transdermal drug delivery," *Journal of Controlled Release* 104:51-66, 2005.
Park et al., "Polymer Microneedles for Controlled-Release Drug Delivery," *Pharmaceutical Research* 23(5):1008-1019, May 2006.
Park et al., "Towards the silicon nanowire-based sensor for intracellular biochemical detection," *Biosensors and Bioelectronics* 22:2065-2070, 2007.
Portnoy et al., "Capacity of Listeriolysin O, Streptolysin O, and Perfringolysin O to Mediate growth of *Bacillus subtilis* within Mammalian Cells," *Infection and Immunity* 60(7):2710-2717, Jul. 1992.
Rossjohn et al., "Structure of a Cholesterol-Binding, Thiol-Activated Cytolysin and a Model of Its Membrane Form," *Cell* 89(5):685-692, May 30, 1997.
Schulz et al., "Peptide-induced antiviral protection by cytotoxic T cells," *Proceedings of the National Academy of Sciences USA* 88:991-993, Feb. 1991.

Silver et al., "Viscoelastic properties of young and old human dermis: A proposed molecular mechanism for elastic energy storage in collagen and elastin," *Journal of Applied Polymer Science* 86(8):1978-1985, Nov. 2002.
Stoeber et al., "Arrays of hollow out-of-plane microneedles for drug delivery," *Journal of Microelectromechanical Systems* 14(3):472-479, Jun. 2005.
Sullivan et al., "Minimally Invasive Protein Delivery with Rapidly Dissolving Polymer Microneedles," *Adv.Mater.*20(5):933-938, Mar. 2008.
Tao et al., "A systematic study of dry etch process for profile control of silicon tips," *Microelectronic Engineering* 78-79:147-151, Dec. 31, 2004.
Tsuchiya et al., "Development of Blood Extraction System for Health Monitoring System," *Biomedical Microdevices* 7(4):347-353, 2005.
Tyagi et al., "Molecular Beacons: Probes that Fluoresce upon Hybridization," *Nature Biotechnology* 14(3):303-308, 1996.
Vigna et al., "Lentiviral vectors: excellent tools for experimental gene transfer and promising candidates for gene therapy," *Journal of Gene Medicine* 2(5):308-316, Sep./Oct. 2000.
Walther et al., "Viral Vectors for Gene Transfer: a Review of Their Use in the Treatment of Human Diseases," *Drugs* 60(2):249-271, Aug. 2000.
Wang et al., "Label-free hybridization detection of a single nucleotide mismatch by immobilization of molecular beacons on an agarose film," Nucleic Acids Research 30(12):e61, 2002, 9 pages.
Wu et al., "Production of viral vectors for gene therapy applications," *Current Opinion in Biotechnology* 11(2):205-208, Apr. 2000.
Yuan et al., "Measuring microelastic properties of stratum corneum," *Colloids and Surfaces B: Biointerfaces* 48(1):6-12, Mar. 1, 2006.
Zheng et al., "Multiplexed electrical detection of cancer markers with nanowire sensor arrays," Nature Biotechnology 23(10):1294-1301, 2005.
Zhou et al., "Liposome-Mediated Cytoplasmic Delivery of Proteins: An Effective Means of Accessing the MHC Class I-Restricted Antigen Presentation Pathway," *Immunomethods* 4(3):229-235, 1994.
International Preliminary Report on Patentability, mailed Jul. 8, 2010, for International Application No. PCT/AU2008/001903, 8 pages.
International Preliminary Report on Patentability, completed Nov. 14, 2012, for International Application No. PCT/AU2011/000890, 6 pages.
International Preliminary Report on Patentability, mailed Jun. 7, 2006, for International Application No. PCT/GB2005/000336, 11 pages.
International Search Report, mailed Feb. 20, 2009, for International Application No. PCT/AU2008/001903, 5 pages.
International Search Report, mailed Oct. 25, 2011, for International Application No. PCT/AU2011/000890, 4 pages.
International Search Report, mailed Feb. 20, 2013, for International Application No. PCT/AU2012/001289, 13 pages.
Widera et al., "Effect of delivery parameters on immunization to ovalbumin following intracutaneous administration by a coated microneedle array patch system," *Vaccine* 24:1653-1664, 2006.
Written Opinion of the International Searching Authority, mailed Feb. 20, 2009, for International Application No. PCT/AU2008/001903, 6 pages.
Crichton et al., "The viscoelastic, hyperelastic and scale dependent behaviour of freshly excised individual skin layers," *Biomaterials* 32:4670-4681, Mar. 2011 (13 pages).
Fernando et al., "Potent Immunity to Low Doses of Influenza Vaccine by Probabilistic Guided Micro-Targeted Skin Delivery in a Mouse Model," *PLoS One* 5(4):e10266, Apr. 2010 (11 pages).
Henry et al., "Microfabricated Microneedles: a Novel Approach to Transdermal Drug Delivery," *Journal of Pharmaceutical Sciences* 87(8):922-925, Aug. 1998 (4 pages).
McAllister et al., "Microfabricated needles for transdermal delivery of macromolecules and nanoparticles: Fabrication methods and transport studies," *PNAS* 100(24):13755-13760, Nov. 2003 (6 pages).

* cited by examiner $X_1 = CH_3$ $X_2 = COOH$
$NH_2$

Carbodiimide
(EDC for aqueous)
(DIC for non-aqueous)

+ NH$_2$-Probe

No probe attached here
(keep surface clean, no
adsorption/capture of biological
materials

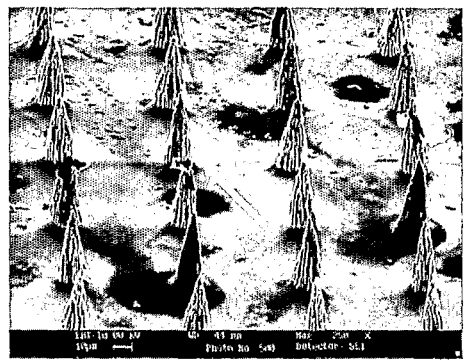
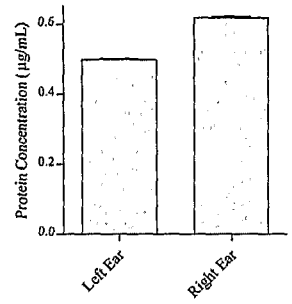
Fig. 9         Fig. 10
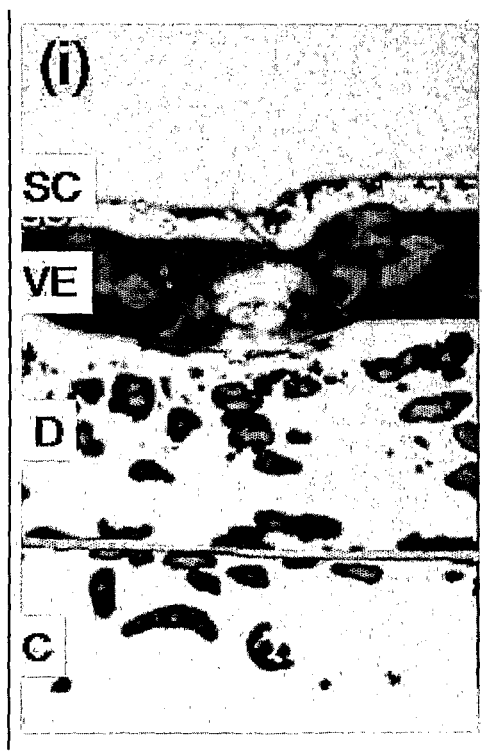
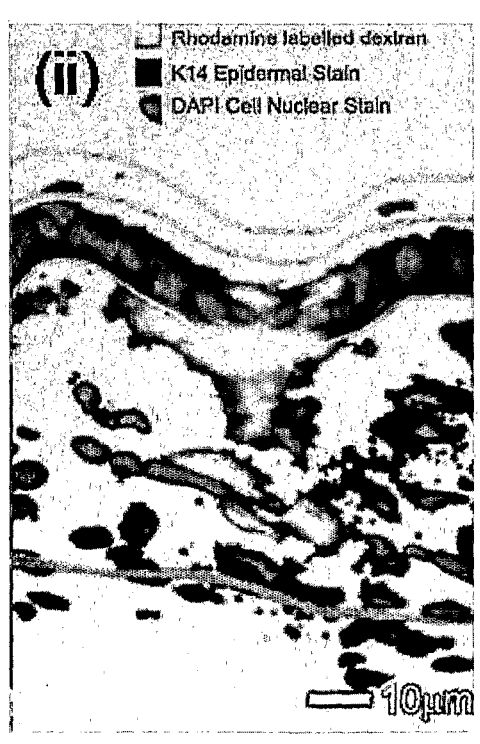
Fig. 11A       Fig. 11B

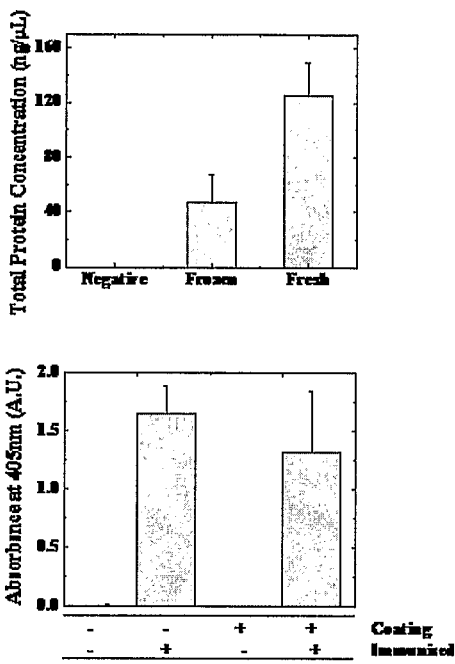
Fig. 12A
Fig. 12C
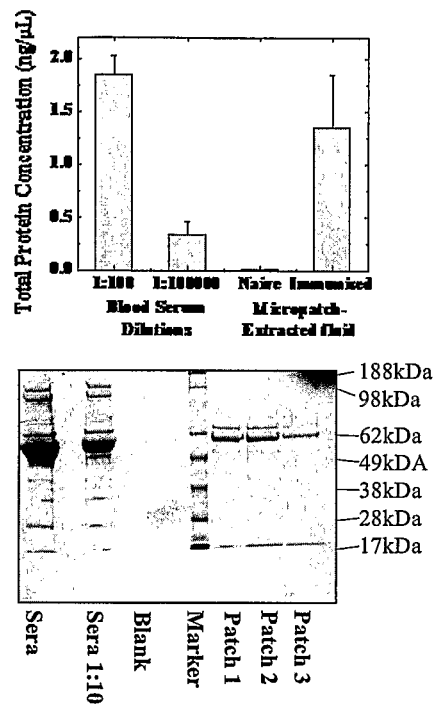
Fig. 12B
Fig. 12D
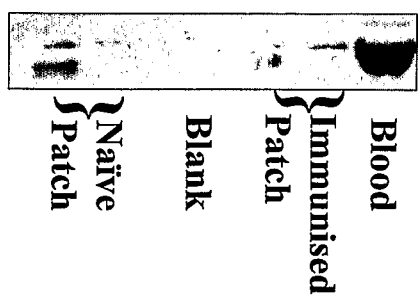
Fig. 13

ANALYTE DETECTION USING A NEEDLE PROJECTION PATCH

BACKGROUND OF THE INVENTION

The present invention relates to a method and apparatus for use in detecting analytes in a subject, and in particular to a patch and method of use thereof in detecting analytes.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Biological markers, such as proteins, antibodies, cells, small chemicals and nucleic acids, whose presence may indicate a diseased state, have been found in blood serum and their levels are routinely measured for research and for clinical diagnosis. Standard tests include antibody analysis for detecting infections, allergic responses, and blood-borne cancer markers (e.g. prostate specific antigen analysis for detecting prostate cancer). The biological markers may originate from all over the body but are extracted from a single location, the venous blood.

However, this is not suitable for all conditions as often blood does not contain key biological markers for diseases originating in solid tissues (or when it finally does, the disease may be too advanced for successful treatment). This problem has been partially overcome by taking tissue biopsies. However, this process is often error-prone, has low sensitivity and involves painful procedures for the patients, as described in Q. Feng, M. Yu and N. Kiviat, "Molecular Biological markers for Cancer Detection in Blood and Bodily Fluids", Critical Reviews in Clinical Laboratory Sciences, 2006, 43, 497-560. It is also time-consuming, costly and can require highly-skilled personnel such as surgeons. Accordingly, alternative diagnostic techniques are therefore desirable.

Another serum-rich fluid is the interstitial fluid (ISF) which fills the intercellular spaces in solid tissues and facilitates the passage of nutrients and excretory products via the blood stream. Studies have demonstrated that ISF has a similar composition to blood serum however there has been relatively little activity in exploring its diagnostic potential.

Microdialysis is the current gold standard for ISF analysis and involves (a) inserting microneedle-based dialysis apparatus into the tissue of interest, (b) equilibrating the dialysate with the tissue environment, (c) extracting fluids over time and (d) analyzing the fluid for specific biological markers using standard chemical analysis techniques (e.g. mass spec, HPLC, etc). Such techniques are described in Anderson C, "Cutaneous Microdialysis: Is it Worth the Sweat?", J. Inv. Dermatol. 2006; 126: 1207-1209, as well as in U.S. Pat. No. 5,353,792, U.S. Pat. No. 6,463,312, U.S. Pat. No. 6,478,738, U.S. Pat. No. 7,169,600, U.S. Pat. No. 7,022,071 and U.S. Pat. No. 5,449,064. However, such techniques typically rely on sampling over an extended time period, which can be inconvenient for the patient. Additionally, these techniques require complex fluid control apparatus for equilibrating the dialysate, and then extracting the fluids, rendering the apparatus and hence the process, expensive.

It is known to provide patches including a number of projections thereon to allow bioactive material to be administered to a subject. Such arrays of projections or needles on a patch are an increasingly effective way of delivering therapeutic since there is minimal or no pain, little or no injury from the needle and highly reduced possibility of cross infection. The solid projections or needles on a patch can be coated with drugs or macromolecules. These can be subsequently delivered to a desired target by the penetration of the projections or needles into the skin.

For example, WO2005/072630 describes devices for delivering bioactive materials and other stimuli to living cells, methods of manufacture of the device and various uses of the device, including a number of medical applications. The device comprises a plurality of projections which can penetrate a body surface so as to deliver the bioactive material or stimulus to the required site. The projections are typically solid and the delivery end section of the projection is so dimensioned as to be capable of insertion into targeted cells to deliver the bioactive material or stimulus without appreciable damage to the targeted cells or specific sites therein.

The use of micro-needle versions of such arrays in sampling fluids is also known. However, the techniques focus on the use of micro-fluidic techniques such as capillary or pumping actions to extract fluid, as described for example in Mukerjee E, Collins S D, Isseroff R R, Smith R L, Sensors and Actuators a-Physical 2004; 114(2-3):267-275, Kazuyoshi Tsuchiya, Naoyuki Nakanishi, Yasutomo, Uetsuji, and Eiji Nakamachi, Development of Blood Extraction System for Health Monitoring System, Biomedical Microdevices, 2005, 7:4, 347-353. Such techniques are also described for example in U.S. Pat. No. 6,923,764, U.S. Pat. No. 6,052,652, U.S. Pat. No. 6,591,124, U.S. Pat. No. 6,558,361, U.S. Pat. No. 6,908,453, and US2005/0261632, US2006/0264782, US2005/0261632, US2005/0261632, U.S. Pat. No. 6,589,202.

However, these systems suffer from a number of drawbacks. Firstly, use of capillary or pumping actions can only be achieved using micro scale projections, as opposed to the smaller scale nano-projections often used in drug delivery. Such micro projections typically pass through the dermis and consequently can end up sampling blood as opposed to interstitial fluid. This can also cause discomfort and irritation to the subject being sampled. Secondly, the requirement for capillary or pumping actions renders the arrays complex, resulting in arrays that are difficult and expensive to manufacture, making them unsuitable for general use.

Other in vitro diagnostic devices are known, such as the use of arrays that include silicon nanowires, or other complex detection mechanisms, such as direct radio-frequency detection of nucleotide hybridization to perform the detection. Again the fabrication of such systems is complex and expensive, again making these unsuitable for practical applications. Examples of this are described in Inkyu Park, Zhiyong Li, Xuema Li, Albert P. Pisano, R. Stanley Williams, "Towards the silicon nanowire-based sensor for intracellular biochemical detection", 2007, Biosensors and Bioelectronics 22:2065-2070, and Zheng G, Patolsky F, Cui Y, Wang W U, Lieber C M, "Multiplexed electrical detection of cancer markers with nanowire sensor arrays" 2005, Nature Biotechnology, 23:10, 1294.

SUMMARY OF THE PRESENT INVENTION

In a first broad form the present invention provides apparatus for use in detecting analytes in a subject, wherein the apparatus includes:
  a) a number of projections provided on a patch, such that applying the patch to the subject causes at least some of the projections to be inserted into the subject and target one or more analytes; and, b) a reagent for detecting the presence or absence of analytes.

Typically a coating is applied to at least some of the projections, the coating including a reagent for reacting with analytes in the subject.

Typically a coating is applied to at least some of the projections, the coating being for extracting analytes when the projections are removed from the subject.

Typically the coating includes a binding agent for binding with analytes of interest.

Typically the coating includes a probe for selectively targeting analytes of interest.

Typically the coating includes a material to repel at least some analytes from the projections.

Typically the material includes a polymer.

Typically the coating includes:
a) a first coating layer for repelling analytes; and,
b) a second coating layer including at least one of:
   i) a binding agent for binding with analytes of interest; and,
   ii) a reagent for reacting with analytes of interest.

Typically, for projections coated with the first coating, the first coating is applied, to substantially all of the projection.

Typically, for projections coated with the second coating, the second coating is applied to a tip of the projection.

Typically the apparatus includes:
a) at least first projections for targeting first analytes; and,
b) at least second projections for targeting second analytes.

Typically:
a) the first projections are coated with a first binding agent; and,
b) the second projections are coated with a second binding agent.

Typically:
a) the first projections have a first geometry; and,
b) the second projections have a second geometry.

Typically the projections are for absorbing analytes.

Typically the projections are for selectively absorbing analytes of interest.

Typically the projections include one or more pores, the pores being adapted to receive analytes.

Typically the pores have a size for targeting analytes of interest.

Typically the projections include a binding agent distributed therein, the binding agent being for binding with analytes of interest.

Typically the projections are at least one of:
a) polymer projections;
b) silicon projections; and,
c) organosilicate projections.

Typically the apparatus includes a housing defining at least one well, wherein in use the at least one well contains a solution including a reagent, such that in use, at least some of the projections can be inserted into the well, thereby allowing the analytes to react with the reagent.

Typically the housing defines a plurality of wells for receiving respective projections.

Typically each well contains a solution including a respective reagent, such that in use, at least some of the projections can be inserted into each well, thereby allowing analytes to react with a number of different reagents.

Typically the patch includes respective areas of projections, each area of projections being for extracting a respective analyte, and wherein the areas are arranged such that each area of projections is inserted into a respective well, thereby allowing different analytes to react with respective reagents.

Typically the projections are configured to target analytes in at least one of:
a) an epidermal layer in the subject;
b) a dermal layer in the subject;
c) a capillary layer in the subject;
d) an epithelial layer; and,
e) any accessible surface layer in the subject.

Typically the length of the projections prevents the projections entering the dermis.

Typically the projections include a support section and a targeting section.

Typically the targeting section has a diameter of less than at least one of:
a) 1 µm; and,
b) 0.5 µm.

Typically a length for the targeting section is at least:
a) less than 0.5 µm; and,
b) less than 1.0 µm; and,
c) less than 2.0 µm.

Typically a length for the support section is <200 µm.

Typically the projections are solid.

Typically the projections are non-porous and non-hollow.

Typically the reagent reacts with analytes to generate a visible indication.

Typically the analytes include at least one of:
a) epigenetic markers;
b) short RNA species;
c) nucleic acids or proteins;
d) antigens, allergens, or adjuvants;
e) parasites, bacteria, viruses, or virus-like particles;
f) immunoglobulins; and,
g) cells.

Typically the apparatus includes:
a) a flexible substrate; and,
b) a number of patches, each patch including a number of projections for penetrating a body surface, the number of patches being mounted to a flexible backing.

Typically the detection of analytes is used in determining the presence, absence or concentration of one or more analytes in the subject.

In a second broad form the present invention provides a method for use in detecting analytes in a subject, wherein the method includes:
a) applying a patch to the subject such that a number of projections arranged on the patch are inserted into the subject and target one or more analytes;
b) removing the projections from the subject; and,
c) using a reagent to determine the presence or absence of analytes.

Typically the method includes:
a) removing the projections from the subject; and,
b) exposing the analytes to the reagent.

In a third broad form the present invention provides a method of producing a patch for use in detecting analytes in a subject, wherein the method includes applying a coating to a number of projections provided on the patch, the projections being arranged such that applying the patch to the subject causes at least some of the projections to be inserted into the subject and target one or more analytes, the coating being for at least one of:
a) for reacting a reagent with analytes in the subject; and,
b) extracting analytes when the projections are removed from the subject.

In a fourth broad form the present invention provides apparatus for use in sampling analytes in a subject, wherein the apparatus includes:

a) a number of projections provided on a patch such that applying the patch to the subject causes at least some of the projections to be inserted into the subject; and, b) a coating applied to at least some of the projections, the coating including a binding agent for binding at least some analytes to the projections, thereby extracting analytes when the projections are removed from the subject.

In a fifth broad form the present invention provides apparatus for use in detecting analytes in a subject, wherein the apparatus includes:

a) a number of projections provided on a patch such that applying the patch to the subject causes at least some of the projections to be inserted into the subject; and, b) a coating applied to at least some of the projections, the coating including a reagent for reacting with analytes in the subject, thereby allowing the presence of analytes to be determined when the projections are removed from the subject.

In a sixth broad form the present invention provides a kit for use in detecting analytes in a subject, wherein the kit including:

a) a number of projections provided on a patch, such that applying the patch to the subject causes at least some of the projections to be inserted into the subject and target one or more analytes; and, b) a reagent for detecting the presence or absence of analytes.

It will be appreciated that the broad forms of the invention may be used individually or in combination.

BRIEF DESCRIPTION OF THE DRAWINGS

An example of the present invention will now be described with reference to the accompanying drawings, in which:—

FIG. 9 is a scanning electron microscopy image of an example of a patch after exposure to human skin;

FIG. 10 is a column graph showing the total protein concentration extracted from mouse ears by uncoated patches;

FIGS. 11A and 11B are inverted fluorescence micrographs showing an example of the extent of projection penetration for targeting the viable epidermis (VE) and dermis (D), respectively;

FIG. 12A is a chart of an example of the levels of protein extraction for different samples;

FIG. 12B is a chart of an example of the amount of AO-IgG recovered from a patch after incubation in naïve and ovalbumin-immunised mice with respect to diluted serum;

FIG. 12C is a chart showing an example of the effect of surface coatings in reducing protein adsorption;

FIG. 12D is a gel electrophoresis image of an example of comparison between protein content in blood and ISF;

FIG. 13 is an example of a western blot with an anti-hemoglobin antibody showing the presence of hemoglobin on a patch applied to a mouse;

DETAILED DESCRIPTION OF THE PREFERRED EMBODIMENTS

An example of apparatus for delivering material to targets within a body will now be described with reference to FIGS. 1A to 1F.

In this example, the apparatus includes a patch 100 having a number of projections 110 provided on a surface 121 of a substrate 120. The projections 110 and substrate 120 may be formed from any suitable material, but in one example, are formed from a silicon type material, allowing the device to be fabricated using processes such as vapour deposition, silicon etching, Deep Reactive Ion Etching (DRIE), or the like. The projections are therefore typically solid, non-porous and non-hollow.

However, this is not essential and alternative materials may be used such as organosilicates (e.g. aminosilanes), polymers, or the like, and alternative manufacturing techniques may also be used, such as molding or the like.

In the example shown, the patch has a width W and a breadth B with the projections 110 being separated by spacing S.

Figure 1A:
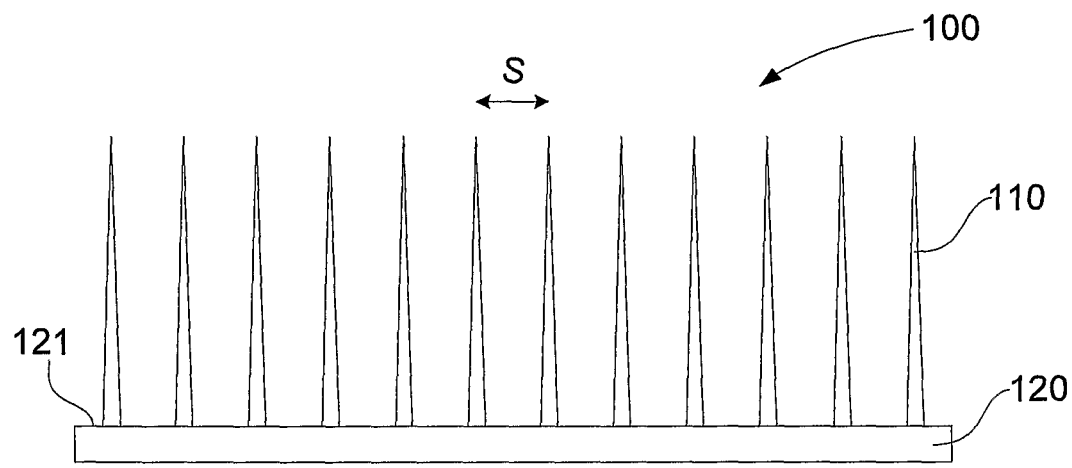
FIGS. 1A and 1B are schematic side and plan views of an example of apparatus for use in detecting analytes in a subject.
Figure 1B:
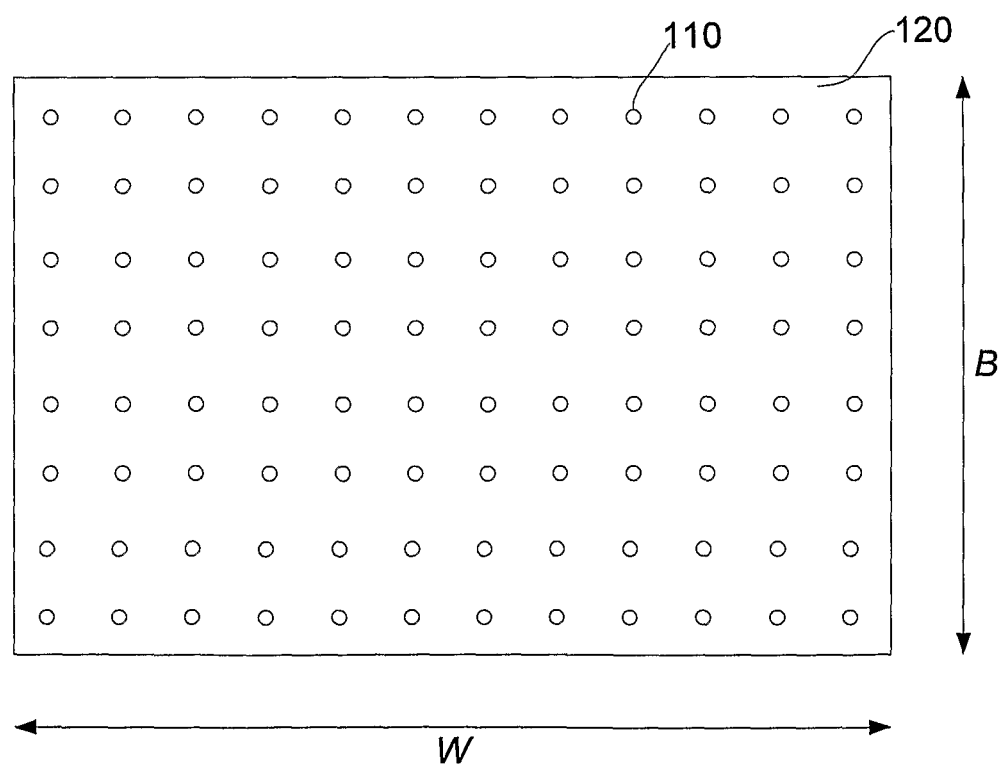
Figure 1C:
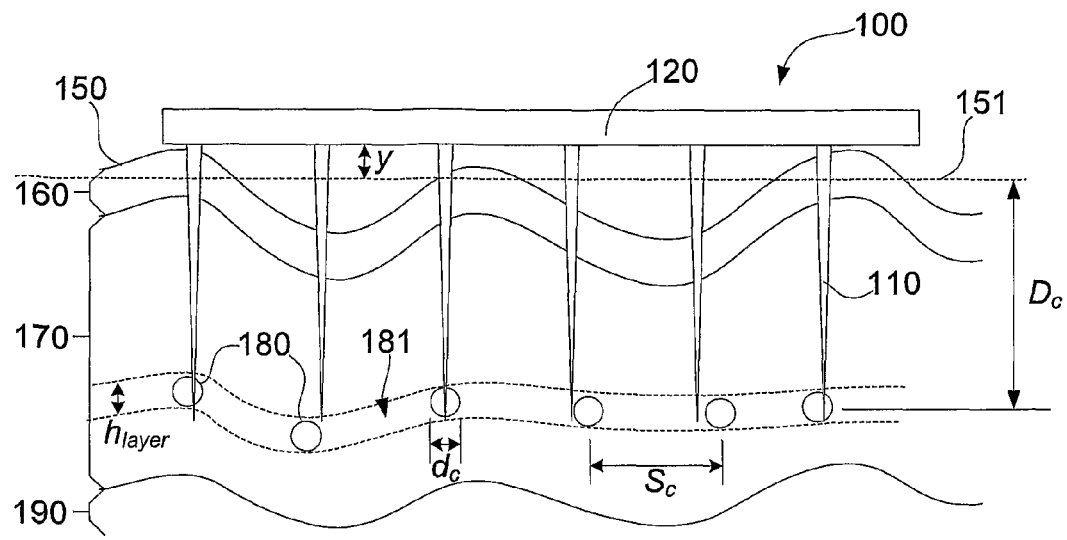
FIG. 1C is a schematic diagram of an example of the apparatus of FIG. 1A in use.

In use, the patch 100 is positioned against a surface of a subject, allowing the projections to enter the surface and detect analytes, such as biological markers, contained therein. An example of this is shown in FIG. 1C. In this example, the patch 100 is urged against a subject's skin shown generally at 150, so that the projections 110 pierce at least the Stratum Corneum 160, and enter the Viable Epidermis 170.

In one example, this allows the projections 110 to contact targets of interest 180, allowing analytes therein to be detected. Alternatively, the projections may merely be required to enter the Viable Epidermis 170, or dermis 190, without the need to contact any specific targets 180. This can be used to allow analytes, such as biological markers in the subject's ISF to be detected. The ISF in different regions and/or depths in the skin can include different analytes. By configuring the projections with an appropriate length, and/or by applying the patch in a controlled manner, this allows the depth of projection penetration to be varied through the epidermis layer 170 and dermis 190. This in turn allows different analytes to be targeted. The projections 110 may also be adapted to enter a lower capillary layer, or other region of the subject, depending on the analytes of interest.

In the example of FIG. 1C the targets 180 are provided in a single layer 181 with each target being approximately a constant depth $D_c$ below the Stratum Corneum 160. In this example, the layer height $h_{layer}$ is therefore approximately equal to the diameter of the targets $d_c$, with the targets separated by a spacing $S_c$. It would be appreciated by persons skilled in the art that in this instance the targets may therefore be Langerhans Cells, or the like. However, alternatively the targets 180 can be dispersed throughout the Viable Epidermis 170, so that the target layer 181 will have a greater height $h_{layer}$. Additionally, the surface 150 includes undulations, resulting in a mean surface level 151 shown by dotted lines, with the patch base 120 resting against the surface 150 at a distance y above the mean level 151. These parameters regarding the location of the targets 180 and the patch 100 can be used to determine the preferred geometry of the projections 110, increasing the chance of analytes of interest being detected.

Figures 1D, 1E, 1F:
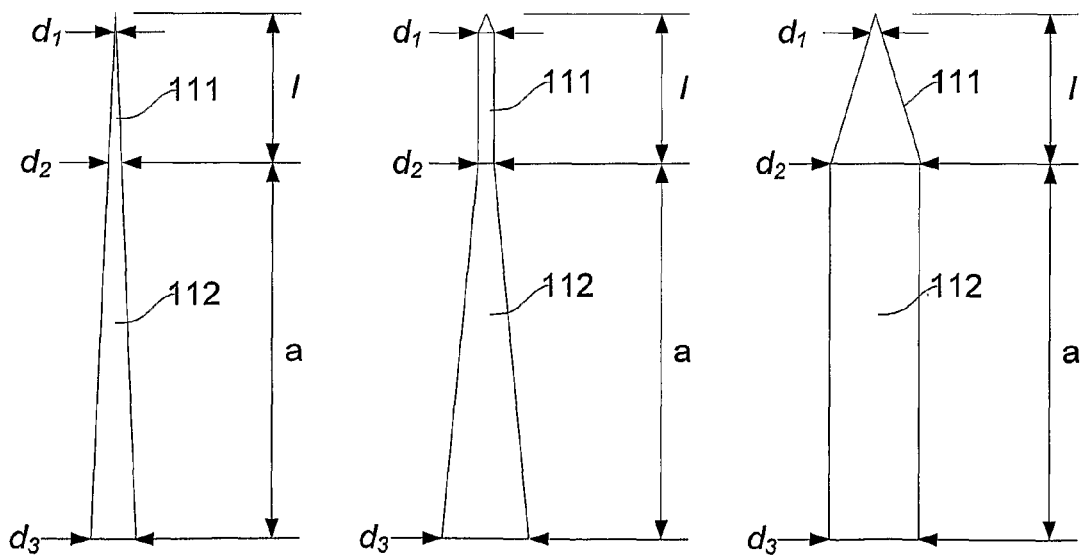
FIGS. 1D to 1F are schematic diagrams of examples of projections used in the apparatus of FIG. 1A.

It will be appreciated that the projections can have a variety of shapes, and examples of suitable projection shapes are shown in more detail in FIGS. 1D, 1E and 1F.

In one example, the projection includes a targeting section 111, intended to target the analytes, and a support section 112 for supporting the targeting section 111. However, this is not essential, and a single element may be used.

In the example of FIG. 1D, the projection is formed from a conically shaped member, which tapers gradually along its entire length. In this example, the targeting section 111 is therefore defined to be the part of the projection having a diameter of less than $d_2$.

In FIGS. 1E and 1F, the structure of the projection may vary along its length to provide a defined targeting section 111 with a designed structure. In the example of FIG. 1E, the targeting section 111 is in the form of a substantially cylindrical shape, such that the diameter $d_1$ is approximately equal to the diameter $d_2$, with a tapered support section, such that the diameter $d_2$ is smaller than the diameter $d_3$. In contrast, in the example of FIG. 1F, the targeting section 111 is in the form of taper such that the diameter $d_1$ is smaller than the diameter $d_2$, with a cylindrical support section, such that the diameter $d_2$ is substantially equal to the diameter $d_3$.

In general, the support section 112 has a length a, whilst the targeting section 111 has a length l. The diameter of the tip is indicated by $d_1$, whilst the diameter of the support section base is given by $d_3$.

In use, the patch 100 can be used to allow analytes to be detected within specific targets within the body, the interstitial fluid (ISF) and/or the blood supply. The patch can also be used to detect analytes within any tissue within the subject and the configuration of the patch will therefore depend on its intended use.

Thus, for example, if the patch is configured so as to ensure that the projections contact specific targets such as cells, then it may be necessary to select a more specific arrangement of projections than if delivery is provided more generally to the blood. To achieve this, the device can be provided with a particular configuration of patch parameters to ensure specific targeting. The patch parameters can include the number of projections N, the spacing S between projections, the projection size and shape, as well as the surface roughness, or any other suitable parameter.

In one specific example, a patch having a surface area of approximately 0.16 cm$^2$ has projections provided at a density of between 1,000-30,000 projections/cm$^2$, and typically at a density of approximately 20,000 projections/cm$^2$. However, alternative dimensions can be used. For example, a patch for an animal such as a mouse may have a surface area of 0.32 to 0.48 cm$^2$, whereas as a patch for a human may have a surface area of approximately 1 cm$^2$. A variety of surface areas can be achieved by mounting a suitable number and arrangement of patches on a common substrate.

The projections 110 typically have a length that depends on the intended use. For example, in detecting analytes in the epidermis, the projections typically have a length of between 10 to 200 µm and typically less than 90 µm. However, the projection length could be less than 1000 µm for analytes in dermal layers, 600-800 µm for basal cells in the epithelium of the mucosa and approximately 100 µm for lung targets. It will also be appreciated that other configurations could also be used, allowing the projections to be used to target analytes in any epithelial or any other accessible surface of the subject. This could include internal surfaces such as organs/vasculature, with this being achieved by mounting the patches on endoscopes or the like.

In addition to projection length, the depth of projection penetration can be also depend on other variables, such as the manner in which the patch is applied, including the velocity and strain rate of the application, and other mechanical properties of the patch.

If distinct targeting section and support sections are provided, the targeting section typically has a diameter of less than 1 µm and more typically less than 0.5 µm. The length of the targeting section is typically less than 100 µm, less than 10 µm and typically less than 5 µm. The projection tips also typically have a radius of curvature in the region of 1 µm or less, although larger curvatures such as 5 µm may be used.

However, it will be appreciated that other dimensions may be used.

Figure 2:
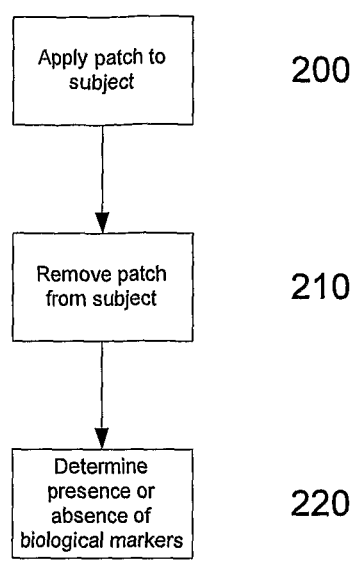
FIG. 2 is a flow chart of an example process for using a patch to detect analytes.

An example of a process for use in detecting analytes will now be described with reference to FIG. 2.

In this example, at step 200, the patch 100 is applied to the subject. In the event that the patch is applied to a subject's skin, this results in the projections 110 entering at least the epidermis 170, as described above.

At step 210, the patch is removed from the subject, allowing the presence or absence of analytes to be determined at step 220. This is typically achieved at least in part using a reagent, which is any compound, composition, molecule, or other marker, that is capable of reacting with, binding with, or otherwise indicating or detecting the presence of analytes, such as biological markers, thereby allowing the presence or absence of the analytes to be detected. It will therefore be appreciated that in one example, the reagent includes a ligand, although this is not essential.

In one example, the projections 110 can be used to extract analytes from the subject, with the analytes being subsequently exposed to the reagent. In the event that the projections are uncoated, the projections will typically extract analytes based on the natural affinity of the patch surface, and this may include a range of different types of analyte. In this example, specific analytes of interest may need to be separated from other analytes, or may need to be specifically targeted by the reagent, thereby allowing the analytes of interest to be detected.

Alternatively, however, the projections 110 may be provided with a coating that assists in extracting analytes of interest. This can be achieved using a binding agent, such as specific probes, provided in the coating, as will be described in more detail below. Additionally, the projections 110 may be provided with a coating that is generally repulsive to biological agents. This can be used to reduce the chance of unwanted analytes being extracted.

A further alternative is for a patch coating to be used to reduce or increase non-specific absorption. Thus, for example, coatings can be used to increase or reduce the hydrophilicity of the patch, and hence the patch wettability. For example, gold coated patches provide a "superhydrophilic" surface, with extremely high wettability, and can therefore increase the quantity of biological material that can be extracted from a subject using the patch.

A further alternative is for the reagent to be provided in a coating on the projections 110, so that the reagent reacts with the analytes within the subject. When the patch 100 is removed from the subject, the results of any reaction between the reagent and analytes can be determined.

In one example, the patch can be inserted into, and then removed from the subject after a short time period, such as a few seconds. Alternatively, the patch may be retained in the subject for a prolonged time period, such as a few minutes, a few hours, or even over a number of days, and this can be used to control the amount of analytes detected, which in turn allows the sensitivity of the detection process to be controlled. This also allows measurements to be performed over extended time periods.

In addition to controlling the patch application duration, other factors regarding patch application can be controlled to influence the ability of the patch to detect analytes. This can include, for example, oscillating or otherwise agitating the patch, to increase the chance of analytes binding to the projections, or reacting with a reagent provided on the projections.

In any event, the above described patch 100 allows analytes to be detected in specific tissue sites in the skin or other parts of a subject's body. In one example, this is achieved by extracting analytes from the subject, allowing for analysis to be performed in vitro. This can be achieved using coated projections allowing specific analytes to be targeted. Alternatively, the analytes can be detected in vivo, using a reagent provided in a coating on the projections.

It will be appreciated that the above described technique can be applied to any form of analyte, including, but not limited to:
  nucleic acids or proteins;
  antibodies, allergens, or adjuvants;
  chemokines or cytokines;
  hormones;
  parasites, bacteria, viruses, or virus-like particles;
  epigenetic markers, such as the methylation state of DNA, or chromatin modifications of specific genes/regions;
  short RNA species including microRNA, siRNA, snRNA, shRNA;
  immunoglobulins; and,
  cells.

In addition to detecting naturally occurring analytes described above, the process can also be used to detect administered analytes, such as antigens, drugs or other medications, or the like.

The effect of different coatings will now be described with respect to FIGS. 3A to 3D.

Figure 3A:
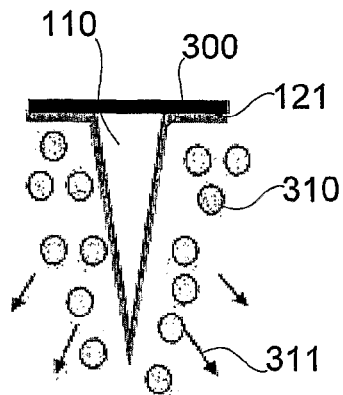
FIG. 3A is a schematic diagram of an example of the effect of coating projections with a polymer to reduce non-specific protein adsorption.

In the example of FIG. 3A, the projections 110 and surface 121 are provided with a coating 300 containing a material that reduces absorption of analytes that are not of interest. Example materials include alkyl groups coated with BSA (bovine serum albumin), bifunctional polyethylene glycol (PEG) polymers, or the like. Such materials have the effect of reducing adsorption of non-specific analytes 310, which are effectively repelled from the projections, as shown by the arrows at 311.

Figure 3B:
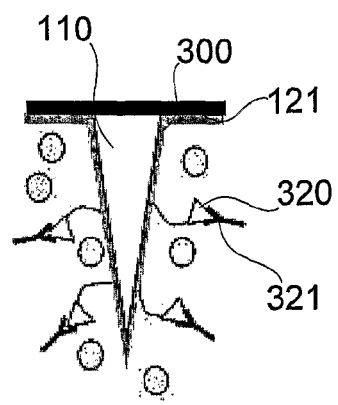
FIG. 3B is a schematic diagram of an example of the effect of coating projections with biological probes which attract and capture specific primary targets.

In the example of FIG. 3B, the projections 110 and surface 121 are additionally coated with a coating including a binding agent, such as one or more probes 320. The probes 320 are designed to target specific analytes of interest 321, which are adapted to bind with or otherwise attach to the probes through an appropriate mechanism. Accordingly, in this example, whilst non-specific analytes 310 are still generally repelled, the specific analytes 321 bind to the probes 320, so that these are captured, allowing for subsequent extraction. This allows the specific analytes of interest to be selectively captured, whilst non-specific analytes remain uncaptured.

Figure 3C:
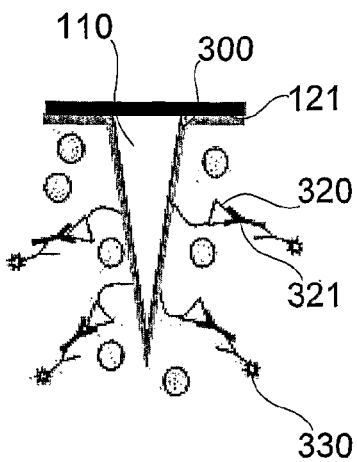
FIG. 3C is a schematic diagram of an example of the effect of incubation of patch with secondary, fluoro-labelled targets.

In the example of FIG. 3C, the analytes 321 captured by the probes 320 are exposed to a reagent 330, such as a secondary, fluoro-labelled indicator. This allows captured analytes 321 to be labelled and subsequently detected using an appropriate detection mechanism, which will depend on the nature of the reagent used. This is typically performed in vitro, once the patch 100 has been removed from the subject.

Figure 3D:
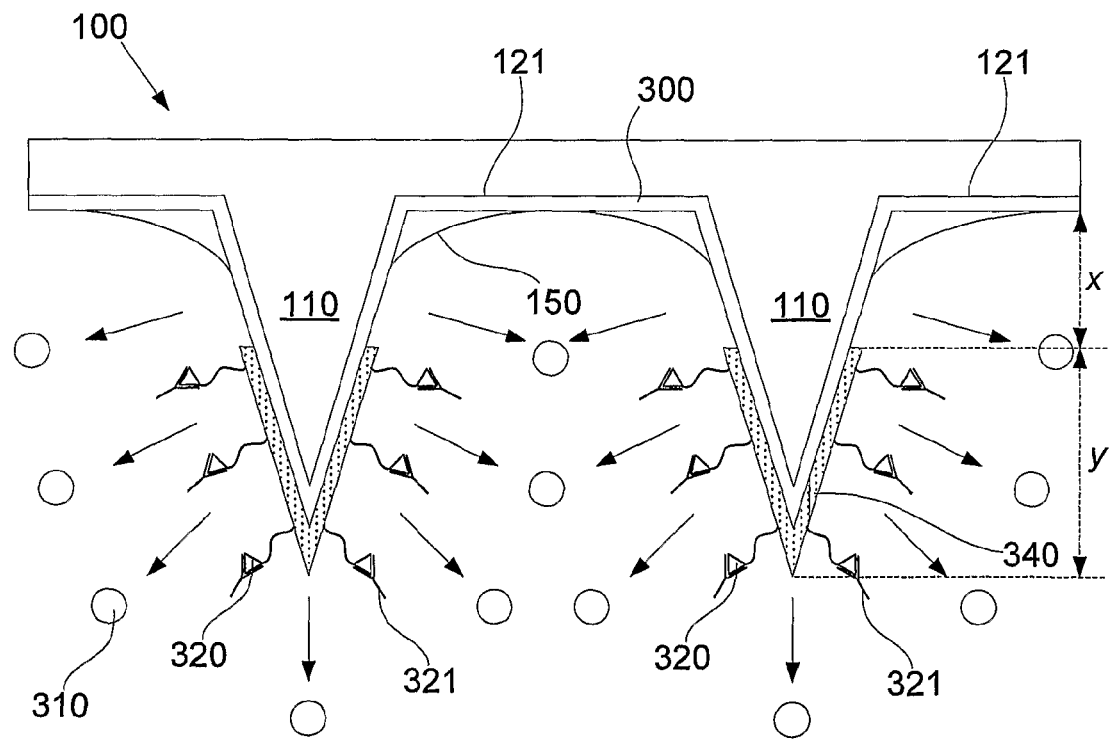
FIG. 3D is a schematic diagram of an example of coating of the projection tip with biological probes.

Whilst probes may be provided in a coating over the entire patch, in the example of FIG. 3D, the probes 320 are provided by providing a coating layer 340 that is only provided on tips of the projections. As a result, probes are attached over a length y of the projection 110, whilst a length x of projection remains probe free. In one example, the length y can correspond to the targeting section 111 of the projections 110, although this is not essential.

By confining the probes 320 to the projection tips, this ensures that analytes of interest 321 are captured on the tips of the projections 110, whilst other regions of the patch 100, such as the surface 121 and a base of the projections 110, remain free of analytes. This in turn allows individual projections 110 to be identified or otherwise resolved when the analytes are subsequently detected.

Identifying individual projections can be useful for a number of reasons. For example, projections can have different sizes, thereby allowing analytes in different regions of the subject, such as in the epidermis and the dermis, to be targeted by different projections. In this instance, by detecting analytes on each projection 110, this allows an assessment to be performed as to from which region of the subject the analytes were collected.

Identifying individual projections 110 also allows different analytes to be targeted by coating projections 110 with different probes 320. Thus, for example, first projections could be coated with a first binding agent, such as first probes, whilst second projections are coated with a second binding agent such as second probes, thereby allowing first and second analytes to be detected.

Additionally, and/or alternatively different projections 110 can be exposed to different reagents, thereby allowing different analytes to be detected. This can be achieved by using a respective projection geometry, such as respective projection lengths, for each of the first and second projections, which can be useful for example if the probes 320 are capable of capturing multiple types specific analytes.

Additionally, in one example, the ratio of uncoated to coated lengths, length x:length y, can be controlled to vary the relative probe loading. This can in turn be used to control the sensitivity of projections to the presence of analytes. Accordingly, by selectively coating projections 110 with different ratios, this can be used to provide a patch 100 having a range of sensitivity, which can in turn be used to determine not only analyte presence, but also an indication of a concentration or amount.

Additionally, or alternatively to using a coating, the ability of the patch projections to target analytes can be achieved by modifying the properties of the projections themselves. In one example, this is achieved using polymer based projections, which can be manufactured using a molding process as will be described in more detail below. In this example, targeting of specific analytes can be achieved using a number of different mechanisms, as will now be described with reference to FIG. 3E.

Figure 3E:
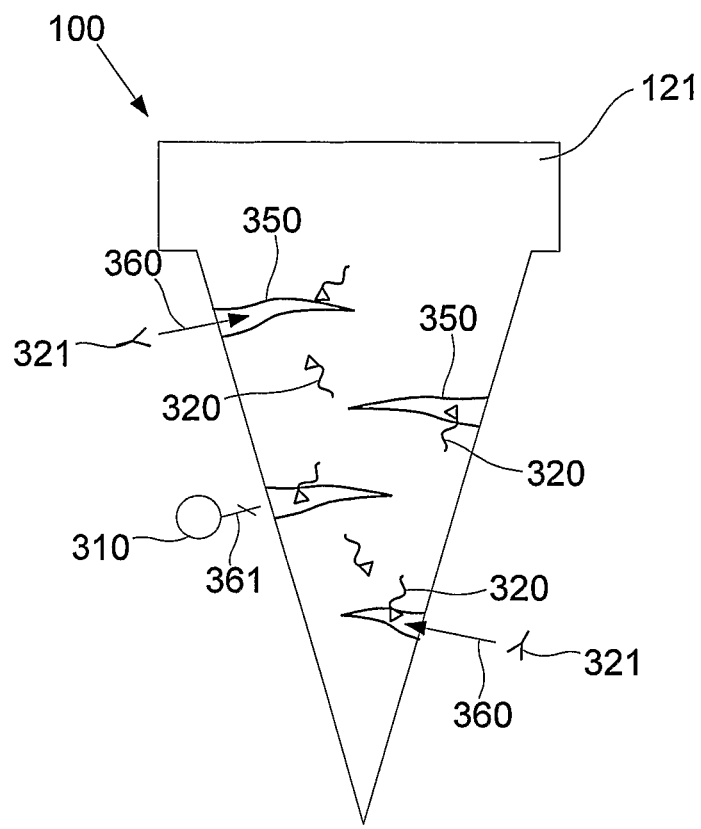
FIG. 3E is a schematic diagram of an example of a projection including pores and embedded probes.

In the example of FIG. 3E, the projections 120 include pores 350 that extend into the projections 110. At a first level the pores can act as a mechanical filter, acting to filter analytes based on the physical size of the analyte. Thus, in this example, the analytes of interest 321 are smaller than the pores 350, thereby allowing the analytes of interest to enter the pores, as shown by the arrows 360. In contrast, other non-specific analytes 310 that are larger than the pores are blocked from entering the pores, as shown at 361. This can provide a degree of specificity to the patch, and in particular can provide a mechanism for allowing at least some course filtering of the analytes targeted by the projections.

An alternative to this is to construct the projections 110 from a material that allows absorption of the analytes in some other manner, such as by diffusion of the analytes into the projection material. In this instance, formation of the projection from an appropriate material can be used to allow for selective absorption, which can in turn be used to select for specific analytes.

Additionally, and/or alternatively, the projections can include a binding agent, such as probes 320, which as in the previous example, can assist with binding of the analytes 321 of interest. In this instance, the probes 320 can be distributed throughout the projections 110, to allow analytes to bind thereto. In this example, analytes can enter the projections via the pores 350, as described above, or through other mechanisms, such as diffusion, or the like, depending on the projection material. It will be appreciated that in a similar manner, any reagent can be incorporated into the projections, and that the use of probes is for the purpose of example only.

Accordingly, it will be appreciated that the use of projections 110 formed from a suitable material can be used to select for analytes.

In any of these examples, this can be used to allow analytes to be removed from the subject for subsequent analysis. However, in the event that reagents are used, the reagents can be used to provide an indication of the presence of analytes, for example through fluorescence or the like, as will be described in more detail below.

In the event that the reagents provide a visible or other similarly detectable indication, such as fluorescence or the like, if the patch is formed from a suitable material that is transparent to the relevant indication, this can allow in-situ detection to be performed, thereby enabling the presence of analytes to be detected whilst the patch is still inserted into the subject. It will be appreciated that this can allow the patch to be used to monitor for analytes over a period of time.

It will also be appreciated that the projections similar to those described above with respect to FIG. 3E may also further include a coating to provide further specificity in the analytes targeted, in a manner similar to that described above.

Figure 4:
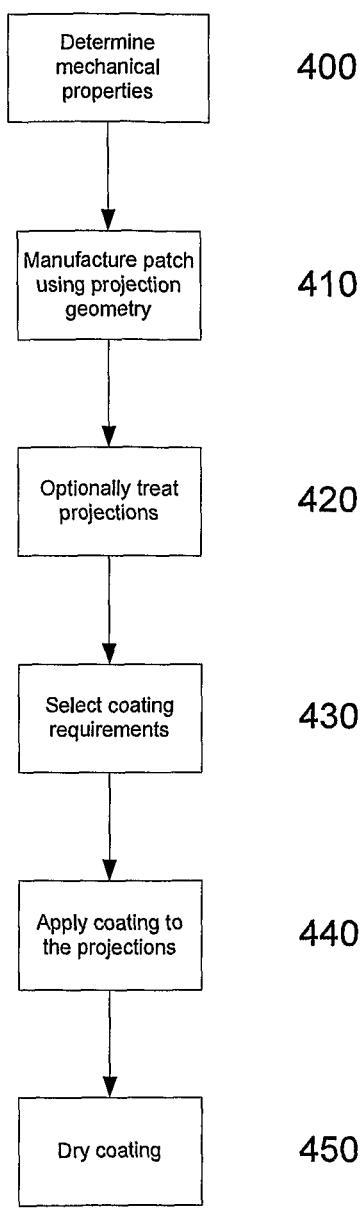
FIG. 4 is a flow chart of an example process for producing a patch for use in detecting analytes.

An example process for producing a patch for use in detecting analytes, will now be described in more detail with reference to FIG. 4.

For the purpose of this example, chemical and mechanical properties of the patches are controlled to maximize extraction of specific analytes from skin of a subject. This will include controlling chemical properties through the use of surface coatings to enhance detection of specific analytes, and mechanical properties such as patch configuration, to target specific regions in the body.

In this example, at step 400, mechanical properties for the patch are determined. Mechanical properties include properties such as projection length, projection shape, patch surface area, surface roughness, projection spacing, or the like.

In general the mechanical properties are selected to increase the overall projection surface area, to thereby increase probe attachment and hence optimise analyte targeting and/or extraction. Patch properties are also optimised for easy insertion and extraction of the projections, as well as to control the hydrophilic/hydrophobic nature of the patch, which is typically determined by the projection spacing and angle.

Figure 5:
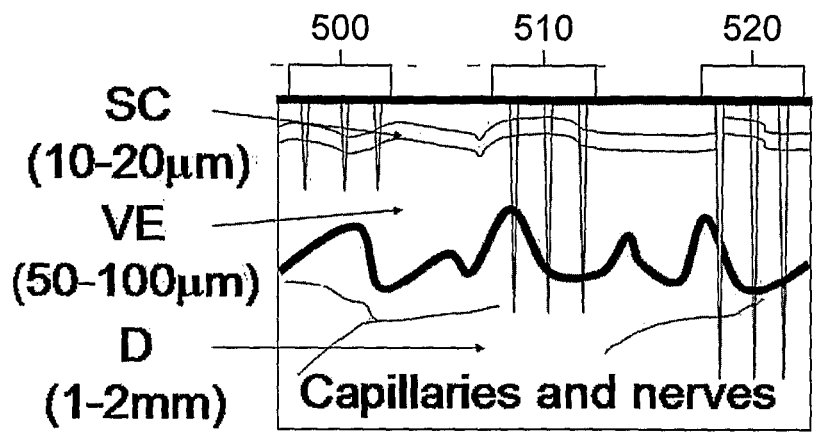
FIG. 5 is a schematic diagram of an example of a patch including projections of differing lengths.

Selection of appropriate mechanical properties, and in particular projection length, can be used to target analytes in different regions within the subject. In general, three main different detection regions can be defined for the skin, as shown in FIG. 5.

In this example, the projections 110 are provided in at three different regions 500, 510, 520, with projections in each of the regions 500, 510, 520 having respective lengths. Typical projection lengths, to penetrate different regions of the skin of a particular human are outlined below, and it will be appreciated that different lengths may be required for different sites on a human, and for different animals.

epidermal penetration for ISF analytes only
(projection length<60 µm);
epidermal and upper dermal for ISF and some blood analytes
(60 µm<projection length<1000 µm); and;
epidermal and deep dermal for ISF and higher blood analyte levels
(1000 µm<projection length<2000 µm).

Example patch properties are described in more detail above with respect to FIGS. 1A to 1F.

Providing epidermal penetration only allows blood-free sampling, which in turn allows a comparison to be performed with blood sera controls. This can be used to distinguish between those analytes that are present only in ISF and are therefore localized to the skin and those that are also found in blood and are therefore systemic (i.e. transported in blood, possibly from other diseased sites). Relative concentrations between ISF and blood analytes can also be used as an indicator of disease progression in some cases.

Providing epidermal and dermal penetration allows analytes in the ISF in both the dermal and epidermal layers, to be detected. In this regard, different analytes may be provided in the different ISF layers, and this can be used to allow these different analytes to be detected. It will also be appreciated that the penetration can be controlled to any depth desired to thereby detect analytes within the ISF at any depth within either of the epidermal or dermal layers.

However, using greater penetration also allows blood to be sampled, thereby allowing a greater range of analytes to be detected using the above described techniques. It will also be appreciated that the device could be used to target analytes in any epithelial or any other accessible surface of the subject.

In one example, different mechanical properties, such as different projection lengths can be selected for different areas of the patch, or different patches. This allows a comparison of analyte concentrations in different regions within the subject, or different analytes to be targeted by different areas on the same patch.

It will therefore be appreciated that the mechanical properties are therefore selected depending on the intended use. An example of determining mechanical properties for delivery of material to selected targets is described in more detail in co-pending application U.S. Ser. No. 11/496,053, and it will be appreciated that similar techniques can be used for detecting analytes associated with selected targets.

At step 410, the patches are manufactured using the determined mechanical properties. This may be achieved in any suitable manner depending on the preferred implementation.

In one example, patch fabrication is achieved using the established deep reactive ion etching (DRIE) process. In this instance, the process typically involves providing a mask on a substrate and etching the substrate using an etchant and a passivant to thereby control the etching process and form the projections.

Whilst any suitable form of etching may be used, in one example, the etchant is typically a compound formed from a group 16 element, such as sulphur, and a halide, such as fluorine. This may therefore include sulphur hex-fluoride ($SF_6$) or the like. The passivant is typically a gas other than oxygen, and in one example includes a group 14 element, such as carbon, and a halide. In one example, the passivant is a per-fluoride hydrocarbon such as octafluorocyclobutane ($C_4F_8$).

The use of suitable etchants and passivants other than oxygen allows for a high degree of control to be provided over the etching process. In particular, adjusting etch parameters such as the passivant to etchant ratio, the gas flow and the etching system operative pressure, this allows etching rates to be controlled with a high degree of accuracy. This in turn allows the degree to which the process is isotropic or anisotropic to be adjusted. By controlling the relative characteristics, this allows the shape of the resulting projections to be carefully controlled.

The etching process may also be paused to allow examination of progress, before subsequent etching is performed. The ability to perform etching in multiple stages in this manner also provides additional control over the resulting projection shape.

The mask may be provided on the substrate using any one of a suitable number of techniques. However, in one example, this is achieved by applying a mask material to the substrate and then selectively exposing the mask material to radiation to thereby form the mask. When passivants other than oxygen are used, the mask material can be formed from an organic photo-resist, such as a crosslinked epoxy resin based polymer. An example of such a material is Su-8 2000 supplied by MicroChem Corp, although other similar related materials can be used. Polymer masks are generally significantly easier to create and use, resulting in the process being significantly cheaper than when a hard mask, such as a metal mask is used.

Following etching, one or more post-etch processes may optionally be performed at step 420, such as chemically sharpening the projections, or applying a metallic layer, such as a gold layer. This can be performed to produce a desired surface for the application of subsequent coatings.

Accordingly, the above described technique allows for the production of silicon, or organosilicate projections to be completed using a combination of optical lithography and deep silicon etching. This allows the profile of the projections to be carefully controlled, thereby allowing projections suitable for use in a range of applications to be created. In general, the above described etching process is suited for manufacturing patches having projections of lengths less than 1000 μm, and is particularly suited for projections suitable for detecting analytes in the epidermis only.

It will be appreciated however, that any suitable patch manufacturing method can be employed, depending on the desired mechanical properties of the patch. For example, in another technique, a silicon etched patch, similar to that described above can be used to create a female mold, for use in creating patches in a molding process. The mold is typically formed from a polymer such as PDMS (Polydimethylsiloxane), although any suitable material may be used.

Following this, the mould is typically filled with a filling material. In one example, this is achieved by providing the filling material in a permeable material, such as a diffusion filter, a polyethersulfone (PES) porous membrane, or the like, before urging the filling material into the mold, for example using a centrifuge or the like. However, this is not essential, and instead the mold may be filled using any suitable technique.

Any suitable filling material may be used, and in one example the filling material is a solution containing a material such as an active compound and/or sugar-based excipient, such as carboxy-methylcellulose (CMC). Alternatively, polymers or the like may be used. It will also be appreciated that the filling material may include any required probes, reagents, or the like that are to be contained within the projections.

Once the mold has been filled, the filling material is solidified. The distribution member can be removed prior to solidification of the filling material, although this is not essential, and alternatively the distribution member may be incorporated into the patch base 120.

The manner in which solidification is performed will depend on the nature of the filling material. Thus, for example, the filling material may be adapted to solidify at room temperature, allowing solidification to occur naturally over time. This can be achieved through the use of a solvent that evaporates at room temperature, or a resin that cures at room temperature. However, alternative mechanisms for solidifying the material may be used, such as:
  exposure to vacuum;
  temperature control;
  humidity control;

using a gas flow;
exposing the filling material to a reagent;
exposing the filling material to UV light; and,
exposing the filling material to radiation, or any other energy source, such as microwave and infrared radiation.

After solidification, the mold is removed from the solidified filling material, with the solidified filling material forming a patch 100 having projections 110 and a base 120 thereby allowing the patch to be extracted from the mold and used.

Depending on polymer material used and the manner in which the curing process is performed the properties of the projections can be controlled. This can be used to selectively target analytes, for example by allowing the curing process to introduce pores into the projections, thereby mechanically controlling those analytes that can be taken up by the projections. Additionally, reagents can be included in the filling material, so that the reagents are present within the projections, allowing analytes to interact with the reagents, for example by transport through pores, or diffusion through the projection material.

At step 430, desired coating properties, such as the nature of the coating, properties of the coating solution and any drying process are determined as required.

The coating and/or the patch mechanical properties can be generally selected to reduce non-specific protein binding, whilst simultaneously increasing the specific capture of specific proteins, such as AO-IgG (anti-ovalbumin IgG), or other anti-IgG antibodies, such as anti-influenza-IgG, or the like. In one example, the coating includes chains of polyethylene glycol (PEG) that repel non-specific protein binding. By using PEG chains terminating in carboxylic acid groups, this facilitates attachment of Protein A or Protein G via standard carbodiimide chemistry. AO-IgG capture probes form strong near-covalent bonds with Protein A/G in the optimal orientation for target binding.

Figure 6A:
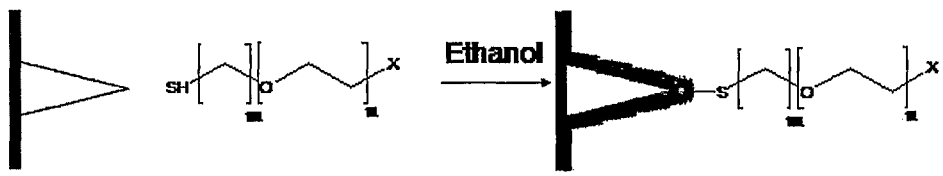
FIGS. 6A to 6C are schematic diagrams of examples of the surface chemistry for different example coatings.
Figure 6B:
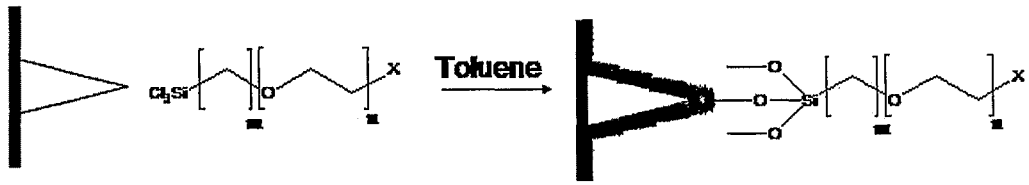
Figure 6C:
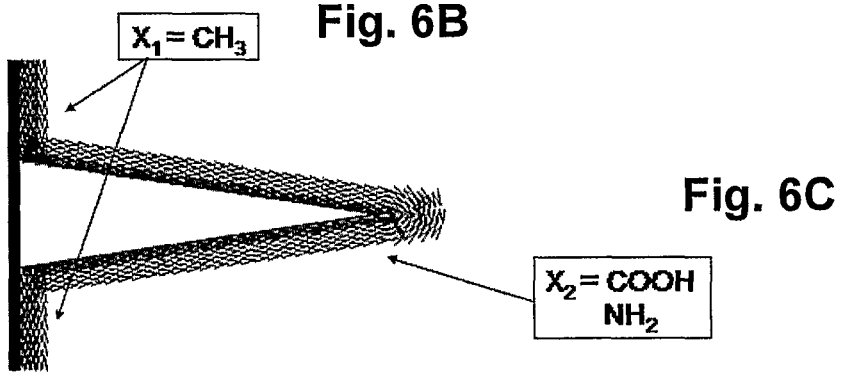

FIGS. 6A and 6B show the preferred synthesis, through the addition of ethanol or toluene, to attach bifunctional polyethylene glycol (PEG) to gold- or silica-functionalized patches. As indicated in FIG. 6C, varying the "X" group of the self-assembled monolayer (SAM) can facilitate the specific localization of biological probes on the projections 110, and more specifically on projection tips, as opposed to on the patch surface 121. This in turn localizes the captured target which can then be identified as being associated with a specific projection, as described above. Localisation of probes to the projection tips may also be assisted by ensuring that the coating containing the probes is only applied to the projection tips. This can be achieved by selection of appropriate coating properties, such as the viscosity and surface tension of the coating solution and/or through the use of an appropriate drying technique, as will be described in more detail below. The biological probes are then attached in aqueous or non-aqueous media. This is performed to ensure that only the projections, and more specifically the projection tips, are coated, whilst at least the substrate surface 121 is uncoated. In one example, this is controlled by positioning of the "X" group of the SAM. Alternatively however, this may be achieved by applying coating solution containing the probes 320, to only the projections, or tips of the projections.

Probes can be attached via a range of standard methods including EDC-mediated crosslinking, glutaraldehyde attachment and Fmoc peptide synthesis.

Figure 6D:
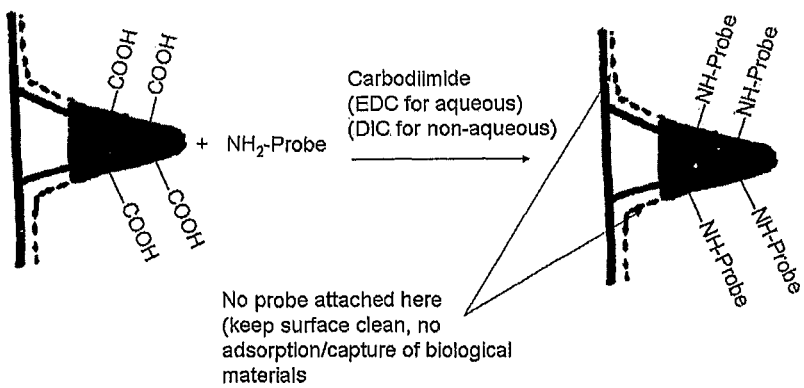
FIG. 6D is a schematic diagrams of examples of probe attachment to coatings.

In one example, probes in the form of proteins specific for various immunoglobulins can be attached as shown in FIG. 6D.

When performing coating, a coating layer is applied at step 440, using any suitable manner such as immersing the projections 110 and optionally the substrate 120, or by applying drops of a coating solution to the projections 110. The coating is then optionally dried at step 450, with this process being performed a number of times, as required, to allow multiple coatings to be provided.

In one example, the coating solution is dried using a gas flow, to thereby remove excess coating solution, and to reduce the drying time. This helps reduce coating solution dispersal from the projections caused by the hydrophobic nature of the patch, and thereby ensure that the projections remain coated as the coating solution dries.

The gas flow could also be provided in a variety of manners. For example, this could be achieved by using a gas jet directed towards the patch. Whilst any gas may be used, in one example the gas is nitrogen as this is substantially inert and will not therefore react with the solution, whilst also being readily available. As an alternative to the use of a gas jet however, flow could be induced by extracting gas from a container containing the patch.

When performing the coating process it is typical to select coating properties, such as gas flow rate, solution properties such as the solution viscosity and surface tension, and optionally a drying time, to thereby control the distribution of coating over the projections 110.

For example, the degree to which the projections are wetted will also depend on the coating solution properties. Thus, for example, if a higher viscosity solution is used, this will tend to adhere more strongly to the projections, and hence allow a greater thickness of coating to be achieved. However, a higher viscosity coating solution may require an increased gas flow to allow adequate distribution over the patch.

In the case of surface tension, if the surface tension is too great, the coating solution will not be effective at wetting the projections, reducing the effectiveness of coating. A lower surface tension will increase the ability of the coating solution to wet the projections, allowing better coating, although too low a surface tension and the coating solution can rest primarily on the surface reducing coating of the projection tips.

The solution properties will also have an impact on the drying process. For example, if a thicker viscosity coating solution is used this reduces the likelihood of coating run-off during the drying process, but may increase the drying time.

The coating solution properties can be controlled through the addition of one or more other agents such as a viscosity enhancer, a detergent or other surfactant, and an adjuvant. These ingredients can be provided in a range of different concentrations. For example, the viscosity enhancer or surfactant can form between 0% and 90% of the coating solution.

A range of different viscosity enhancers can be used and examples include methylcellulose, carboxymethylcellulose (CMC), gelatin, agar, and agarose and any other viscosity agents. The solution typically has a viscosity of between $10^{-3}$ Pa·S and $10^{-1}$ Pa·S. In one example, using a coating solution containing 1-2% methylcellulose, which results in suitable uniform coatings, resulting in a viscosity within the range 0.011 (1%)-0.055 (2%) Pa·S.

Similarly, a range of different surfactants can be used to modify the surface tension of the coating solution, such as any detergent or any suitable agent that decreases surface tension, and that is biocompatible at a low concentration. The solution properties are also typically controlled through the addition of one or more other agents such as a viscosity enhancer, a detergent or other surfactant, and an adjuvant. These ingredients can be provided in a range of different concentrations.

For example, the viscosity enhancer or surfactant can form between 0% and 90% of the coating solution.

Additional control is also achieved using the gas flow rate. Thus, a higher gas flow rate can increase the degree to which coating solution is distributed on the patch, and/or can reduce the drying time.

Appropriate selection of the coating properties can be used to ensure at least the projections are coated, as well as to allow the thickness of coating on the projections to be controlled. This can also be used to vary properties such as the relative amounts of coating on the patch surface 121 and on the projections 110, which can be characterised by a coating ratio based on a ratio of an amount of coating on the projections 110 against an amount of coating on the patch surface 121.

The degree to which the patch is hydrophobic will depend on the patch configuration and in particular, on patch parameters such as the projection size and shape and the projection spacing S. Accordingly, when performing a coating process, it is typical to first determine patch properties and then use this information to allow appropriate coating properties to be selected.

The above described fabrication process allows chemical and mechanical properties to be selected that enable extraction of the largest volume of ISF with the lowest non-specific analyte adsorption.

As an alternative to using a coating technique, reagents can alternatively be embedded within the patches. Thus, for example, in the case of molded patches manufactured using a polymer material, the reagent can be introduced into the mold together with the polymer material so that the reagent is distributed throughout the projections. In this example, the polymer can be arranged so that pores form within the projections during the curing process.

In use, the captured analytes can be identified in any one of a number of manners, depending on the preferred implementation, and examples of this will now be described with reference to FIGS. 7A and 7B.

Figure 7A:
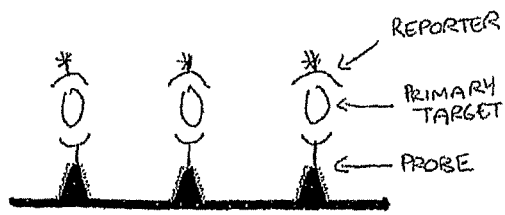
FIG. 7A is a schematic diagram of an example of detecting primary target analytes bound to probes using a labelled reporter molecule.

In the example of FIG. 7A, a sandwich assay is used, in which a target analyte, such as a nucleic acid, binds specifically to projection-bound probes, with detection of the analyte being via a reagent, such as capture of a labelled reporter molecule which specifically binds to the target, but not to the probe. The reporter molecule can be detected using any suitable technique, such as fluorescence, or the like.

Figure 7B:
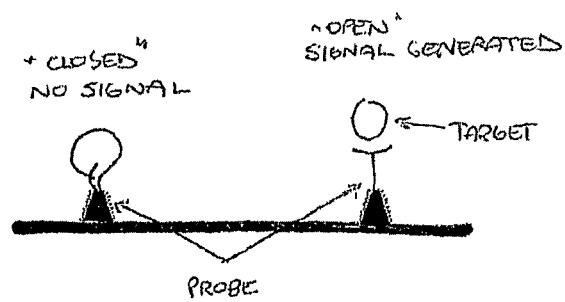
FIG. 7B is a schematic diagram of an example of detecting primary target analytes via a detectable change in the status of the probe molecules.

Alternatively, however, as shown in FIG. 7B, target binding can also occur via a detectable change in the status of the probe. In this example, capture of an analyte leads to the probe being in a "closed" position, whilst a probe without a captured analyte results in the probe being in an "open" position. Accordingly, in this example, the probe acts as a reagent provided in the coating, so that the presence of analytes can be determined when the patch is extracted from the subject. This can be achieved in any suitable manner.

One example of probes that can function in this manner are molecular beacons, which are nucleic acid probes that are labelled with a fluorescent dye at one end and a quencher at the other end. The 6-10 bases at either end of the nucleic acid sequence are complimentary to each other ("stem region"), such that the sequence forms a hairpin loop which brings the quencher/fluorophore in close proximity thus reducing signal. However, a probe sequence specific to a target nucleic acid can be inserted in between the "stem" sequences, such that when a target nucleic acid binds, the beacon is opened and linearised, such that the fluorophore is not inhibited by the quencher and a signal is produced. This avoids the need for a separate reagent to detect the analyte of interest, as the reagent, in this case the fluorophore, is effectively integrated into the coating.

Examples of suitable probe arrangements are described in more detail in Tyagi S., Kramer, F. R., "Molecular beacons: Probes that fluoresce upon hybridization", Nature Biotechnology, 1996, 14(3):303-308, and Wang, H., Li, J., Liu, H. P., Liu, Q. J., Mei, Q., Wang, Y. J., Zhu, J. J., He, N. Y., Lu, Z., "Label-free hybridization detection of a single nucleotide mismatch by immobilization of molecular beacons on an agarose film", Nucleic Acids Research, 2002, 30(12):e61

In the example of FIG. 7A, the patches are applied to a subject's skin and incubated for as long as is required to facilitate specific capture of immunoglobulins to the projections. The patch is then removed and incubated in a vessel containing the fluorescently-labelled secondary target which binds only to those projections. In this example, a high resolution fluorescence scanner can be used to excite the patch 100 and record the emission profile for all projections 110 over the extent of the patch 100, thereby allowing a 2 dimensional image of the patch 100 to be created. In this example, by capturing analytes on tips of projections 100 only, this allows individual projections to be resolved. Furthermore, by capturing different analytes on different projections, this allows specific analytes to be identified, based on known probe locations. This allows the patch to act as a 2-dimensional analyte detection array.

Figures 8A, 8B:
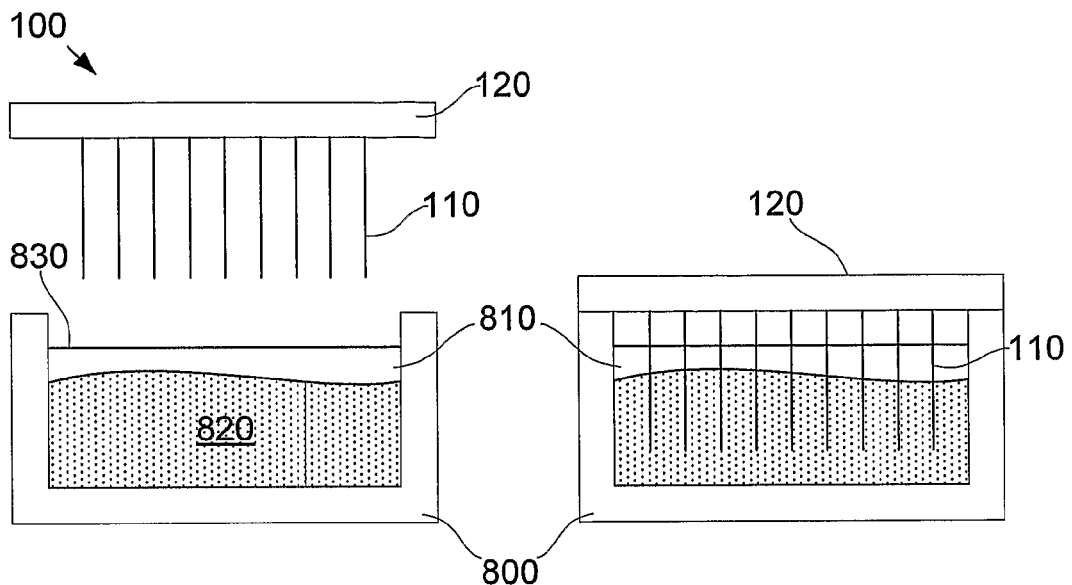
FIGS. 8A and 8B are schematic diagrams of an example of a well for immersing patch projections.

An example vessel for use in applying a reagent to the projections will now be described with respect to FIGS. 8A and 8B.

In this example, the vessel includes a housing 800 defining a well 810 containing a solution 820 including the reagent. This allows the projections to be inserted into the well 810, as shown in FIG. 8B. Following insertion of the projections 110, the solution can be agitated to ensure thorough exposure of the analytes to the reagent.

In one example, the housing is transparent to detection, such as fluorescence scanning, to be performed with the patch retained in the vessel. If other indicator reagents are used however, different sensing may be employed. For example, a conductivity of the solution may be indicative of the amount of recovered analyte, in which case the well 810 may include other sensing means, such as electrodes, which allow a conductivity measurement to be performed.

In one example, the substrate 120 engages the housing 800, for example using a clip fit, friction fit, or the like. By providing a sealing engagement, this assists with agitation of the solution. Additionally, this can be used to allow the housing 800 and patch 100 to be disposed of as a single unit, with the sampled analytes and solution contained. This can be useful in disposal of potentially contagious or otherwise hazardous analytes.

In one example, the solution can be retained in the well using a piercable film 830, so that the well can remain sealed until projections 110 are inserted into the solution 820 through the film 830, in use. This can make the vessel suitable for use in remote regions, by ensuring that the solution remains free of contaminants until required.

Figure 8C:
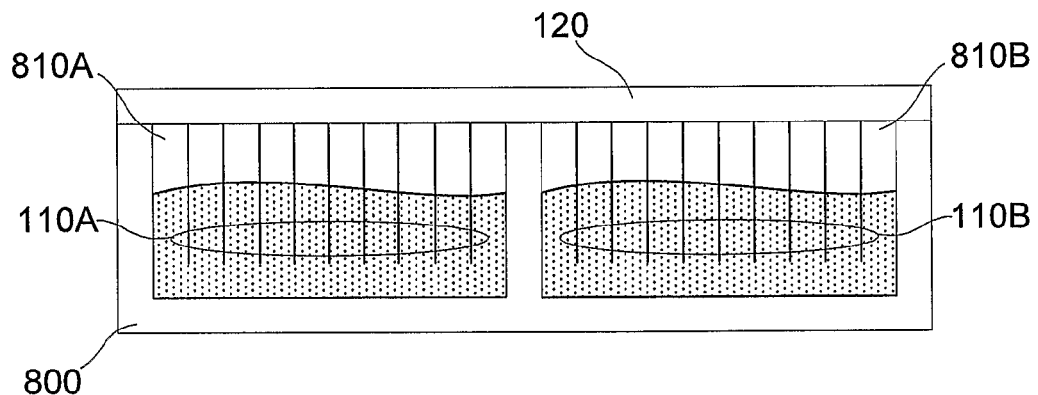
FIGS. 8C and 8D are schematic diagrams of an example of a well array for immersing patch projections.
Figure 8D:
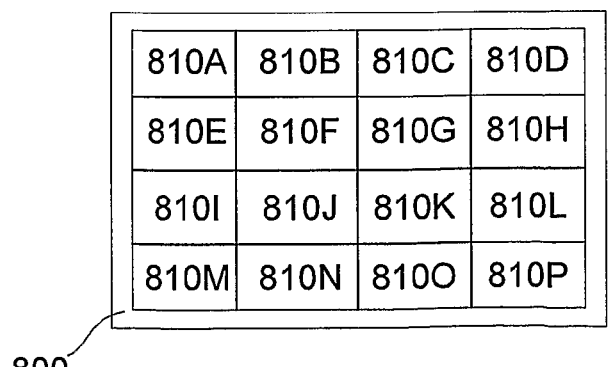

In an alternative example of FIGS. 8C and 8D, the housing 800 defines a number of wells 810A, 810B, . . . 810P each containing a respective solution 820 including a respective reagent. In this example, respective first and second projections 110A, 110B, are adapted to be inserted into respective wells 810A, 81B, allowing tests to be performed for a number of different analytes.

In this example, the projections in each of the respective areas may include different coatings and/or projection configurations for targeting respective analytes, as described above. This allows the patch areas to provide a two dimensional array based test that can detect a number of different analytes.

In one example, as it can be difficult to selectively coat or manufacture different projections on a single patch. Accordingly, a number of patches, each having respective properties or detection capabilities, may be provided on a common flexible substrate, thereby allowing a two dimensional array to be provided using multiple patches.

A number of example experiments will now be described.

Experiment 1

Projection patches were applied to the arms of human volunteers, and a scanning electron microscopy image of a patch after insertion is shown in FIG. 9. This illustrates that projection patches are capable of retaining biological material for analysis without any chemical or mechanical optimization for the purpose. For example, the arrow points to corneocytes removed from the skin of a volunteer, and the black markings on some projections are indicative of extracted interstitial fluid.

Experiment 2

Projection patches with projections having a length of 90 µm were applied onto ears of a live mouse for 60 seconds and then transferred into a phosphate-buffered saline (PBS) solution, using sonication to force biological material off the patch and into suspension.

The total protein concentration was detected via the standard Bradford assay using a UV-VIS spectrophotometer. The results in FIG. 10 show similar protein concentration from both ears of a mouse with respect to a patch unexposed to skin. As a theoretical comparison, a patch containing total monolayer coverage of albumin (most abundant serum protein) would produce 0.5-2 µg/mL depending on the protein stacking geometry, which is comparative to the data.

This demonstrates the ability of an uncoated patch to extract and identify protein from the skin.

Experiment 3

Patches having projection lengths of 60 µm were applied using a quasi static (~0 m/s) and higher velocity (~1 m/s) application onto ears of a mouse. Inverted fluorescence micrograph showing the extent of projection penetration (using rhodamine-labelled dextran) in the (i) viable epidermis (VE) and (ii) dermis (D) are shown in FIGS. 11A and 11B respectively.

Experiment 4

ELISA assays (Enzyme Linked ImmunoSorbent Assay) on patch-extracted fluids were analysed to determine if a particular protein could be detected without specific patch coatings.

In this example, a patch 100 is used with no surface coating is used in the protocol set out below:
  1. Vaccinate mice with ovalbumin to boost antibody response (n=4)
  2. Perform standard ELISA assays on blood to identify antibody response after vaccination.
  3. Insert un-coated patches into ears of the same mice to extract ISF
  4. Perform ELISA assays on patch-extracted fluids
  5. Compare results to identify if antibodies can be detected using standard chemical methods combined with patch extraction Patch-extracted fluid from immunized mice yielded significantly higher anti-ovalbumin IgG concentrations in comparison to the negative control (Naïve mice), as shown in FIG. 12A.

FIG. 12B shows that AO-IgG was detected in patch samples from mice immunised with ovalbumin (n=4 mice). Equivalent samples from non-immunised mice (n=4) yielded no signal in the ELISA assay, as compared to the negative control (lacking a patch sample). These results demonstrate that patches can extract significant quantities of specific antibodies without any chemical or mechanical optimization and that the patch-extracted samples contain significant amounts of a model analyte (AO-IgG).

These results show that patches can be used to extract sufficient material from the epi/dermis to obtain specific ELISA results for particular proteins. However, the interaction between the patch and the sample fluid is non-specific, such that other proteins bind to the patch as well.

Experiment 5

Using the same protocol as experiment 4 above, patches were tested that included a coating designed to reduce non-specific protein binding. Patches were incubated in a Petri dish for 6 hours in a 1 mM ethanedithiol solution in ethanol. After the formation of an alkylated surface (not confirmed), the patches were washed in PBS (containing 1 mM dithiothreitol, DTT) and subsequently incubated overnight in a PBS, DTT solution containing 5% bovine serum albumin (BSA). The BSA binds strongly to the hydrophobic alkylated surface, such that the number of available sites for non-specific protein binding on the patch are minimized.

The same mice were used as in experiment 4. The results, shown in FIG. 12C, indicate that the ELISA signal intensity for the coated patches was lower than that for the uncoated patches (after extracting fluid from immunised mice), thereby demonstrating a reduction in non-specific binding.

Experiment 6

Similar to the experiment 5 above, total protein analysis was performed using a different assay (Q-bit, Invitrogen) and also an SDS-PAGE gel was run to analyse the composition of ISF with respect to serum.

Uncoated patches were inserted into the ears of a live mouse for 60 seconds and then transferred the patches directly into a phosphate-buffered saline (PBS) solution. The insertion and rinsing method was repeated 10 times to maximize protein recovery. Samples were sonicated briefly to dislodge biological material into solution then, with no further processing, the total protein concentration of the solution was detected by a fluorescent assay (QBit, Invitrogen) and quantified by fluorimetry. Samples drawn from different mice (n=3) were reproducible as shown in FIG. 12A, although freezer storage of samples (several days) results in some protein degradation. The difference in apparent concentration in comparison to those results in experiment 2 are likely due to the differences in the experimental protocol (i.e. more insertions used, sonication rather than vortexing) but may also be due to inherent differences between the Bradford and Q-Bit assays or the state of protein degradation.

To compare the protein content of ISF with that of blood serum from the same animal, one-dimensional gel electrophoresis (1DGE) analysis was performed using Coomassie Blue (G-250) detection. The gel presented in FIG. 12D suggests that the ISF contains the same high-abundance proteins as in blood serum (most likely transferring 62 kDa, albumin 49 kDa, SeeBlue protein marker, Invitrogen) and with a more sensitive staining technique, very faint bands may be more apparent.

The results indicate that projection patches can sample quantifiable amounts of total protein via spectrophotometric analysis without surface modification, such as coating. Specific proteins can be detected by ELISA analysis of patch-extracted fluids, indicating that ISF contains some of the same proteins as present in blood serum.

However, coating of the patches can significantly increase selectively. In one example, coating with alkyl groups and BSA reduces non-specific binding, whilst probes can be used to target specific analytes.

Experiment 7

Similar to the experiment 6 above, analysis was performed using a western blot with an anti-hemoglobin antibody, and the resulting data is shown in FIG. 13. If hemoglobin is present in the sample, the antibody will bind specifically and there will be a band in the gel.

The data suggests that patch-extracted samples from both immunised and naïve mice contained hemoglobin, thus indicating that projections were penetrating the epi/dermal barrier and sampling blood, most likely from the dermal papillae.

Experiment 8

C57 mice were injected with either ovalbumin or a flu vaccine, such as FluVax, which is a vaccine currently used for human influenza vaccination and is altered each year to ensure up-to-date protection from the most recent strains of influenza.

After several weeks, 60 mm patches were inserted into the ears of anesthetized mice for 20 s under moderate force, including a group of naïve mice (n=4). After rinsing the patch in 200 ml PBS, the process was repeated 5 times per ear. At the end of the procedure, the patch was left in the PBS solution and sonicated for 5 minutes to remove material attached to the patch. Patches were then removed and the solutions centrifuged at 10,000 g to pellet and remove insoluble material.

Figure 14A:
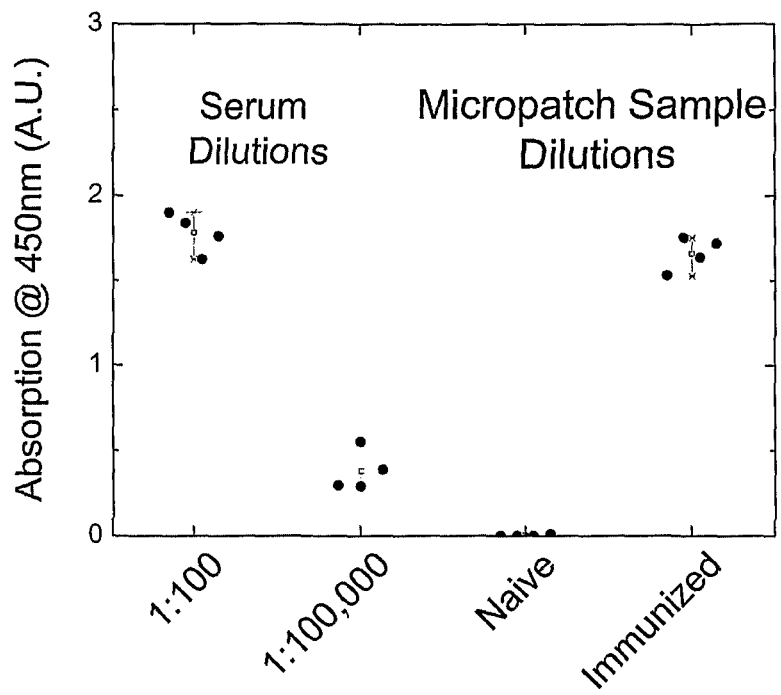
FIG. 14A is a chart of an example of ovalbumin study data for a patch after incubation in naïve and ovalbumin-immunised mice with respect to diluted serum.
Figure 14B:
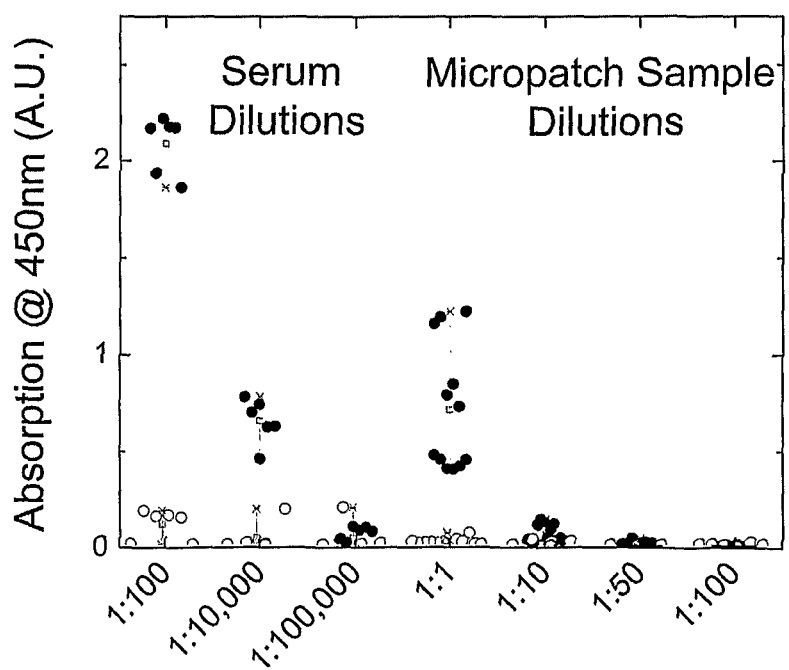
FIG. 14B is a chart of an example of an influenza study data for a patch after incubation in naïve and vaccine-immunised mice with respect to diluted serum.

The samples were then analysed via an indirect ELISA assay using either ovalbumin or influenza antigen, pre-adsorbed to maxisorb plates. The plates were blocked for at least 2 hrs in a 1% BSA/PBS solution followed by thorough rinsing and incubation with patch-extracted samples and blood serum controls, and the results are shown in FIGS. 14A and 14B, respectively.

Once again, the blood serum and patch-extracted samples from immunised mice showed high levels of total anti-influenza-IgG (AI-IgG) in comparison to both negative controls and samples extracted from naïve mice. Interestingly, there was some non-specific signal from undiluted naïve serum controls, however not from the equivalent patch samples. Patch samples from immunized mice diluted from 1:1-1:50 were significantly higher (t-test with p-value=0.05) than the equivalent naïve animals, suggesting a degree of sensitivity comparative to that of blood samples diluted 1:10,000-1:100,000-fold.

Experiment 9

This experiment relates to a protein analysis to demonstrate the effectiveness of the patch in extracting material from a subject.

Six patches were applied to a group of three naïve mice (two patches per ear), blood was withdrawn and the samples pooled and diluted in an appropriate buffer for 2D gel electrophoresis analysis (7M urea/2M thiourea/4% CHAPS/40 mM DTT).

Figure 15A:
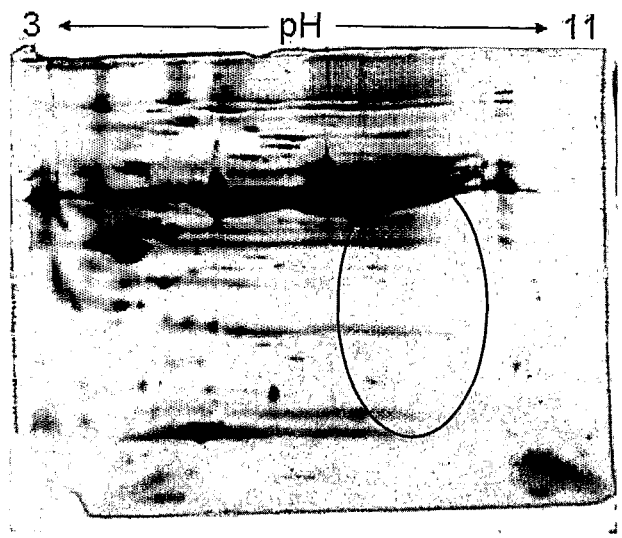
FIG. 15A is an example of a 2D gel electrophoresis analysis image showing the protein content of mouse serum.
Figure 15B:
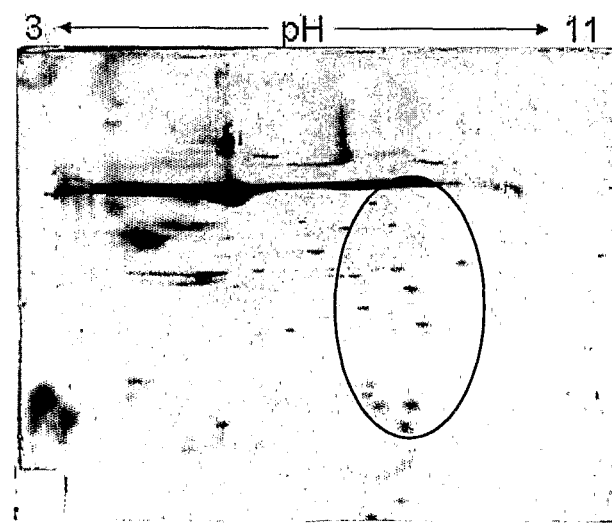
FIG. 15B is an example of a 2D gel electrophoresis analysis image showing the protein content of fluid extracted from mice using a patch.

FIG. 15A shows the protein content of mouse serum, whilst FIG. 15B shows the protein content of fluid extracted from the mice using the patch. The gels show qualitatively that serum and patch-extracted fluids have a similar protein content due to the similar location (and therefore identity) of protein spots across the gels. However, there are a number of proteins present in the patch-extracted fluid sample which are not present in serum, suggesting the presence of unique tissue-specific biomarkers.

Experiment 10

This experiment demonstrates the Non-Specific (NS) binding of Cy5-Ovalbumin to patches. In this regard, to enable specific analyte detection, it is useful to maximize specificity for the biomarker of interest whilst minimizing adsorption of other material to the patch surface.

In this experiment a layer of thiolated polyethylene glycol (5000 MW polyethylene glycol containing a terminal thiol group and a terminal carboxylic acid on the opposite end) is applied to a gold coating on the patch projections. The thiolated polyethylene glycol is chemisorbed to the gold layer via well-described gold-thiol chemistry to form polyethylene glycol (PEG) patches.

The PEG-patches are then exposed to a dilution series of Cy5-labelled ovalbumin protein (range $10^{-7}$-$10^{-10}$M and negative control) and examined by both X-Ray Photoelectron Spectroscopy (XPS, sensitive to the top several atomic layers of a surface) and a fluorescent laser scanner.

Figure 16A:
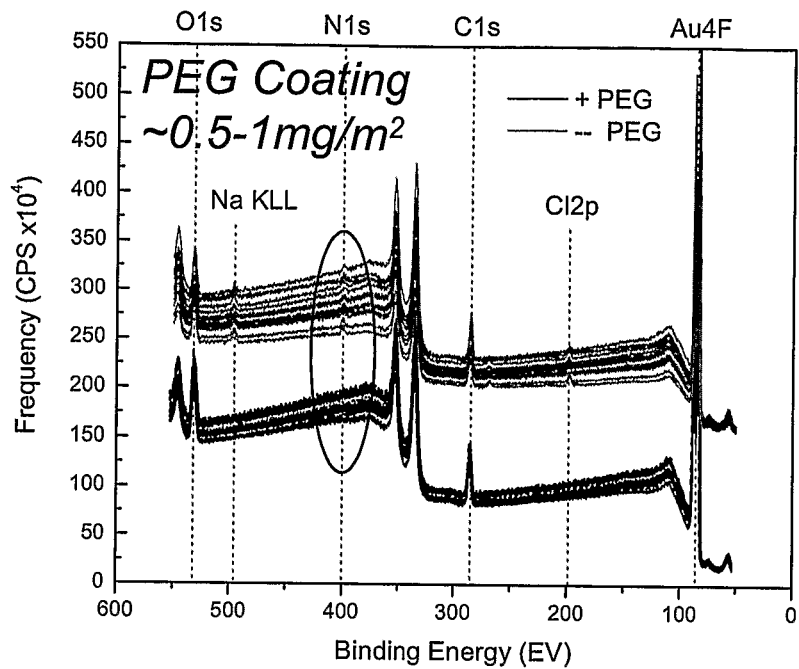
FIG. 16A is an example of X-Ray Photoelectron Spectroscopy (XPS) spectra for coated and uncoated patches exposed to a dilution series of Cy5-labelled ovalbumin protein.
Figure 16B:
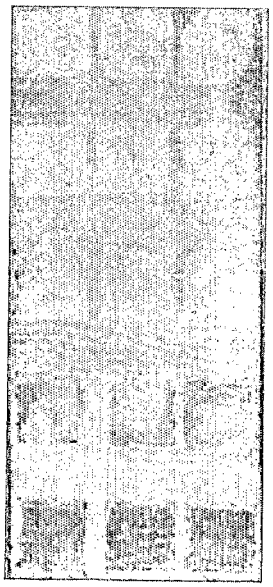
FIGS. 16B and 16C are examples of fluorescent laser scanning analysis images for coated and uncoated patches exposed to a dilution series of Cy5-labelled ovalbumin protein.
Figure 16C:

The XPS spectra shown in FIG. 16A revealed the presence of nitrogen (i.e. from ovalbumin) only for patches without any PEG coating, whilst PEG-patches showed significant nitrogen. This is confirmed by direct analysis of the Cy5 dye via fluorescent laser scanning analysis, as shown in FIGS. 16B and 16C (which are negative images for clarity), for the uncoated and PEG patches respectively.

Figure 16D:
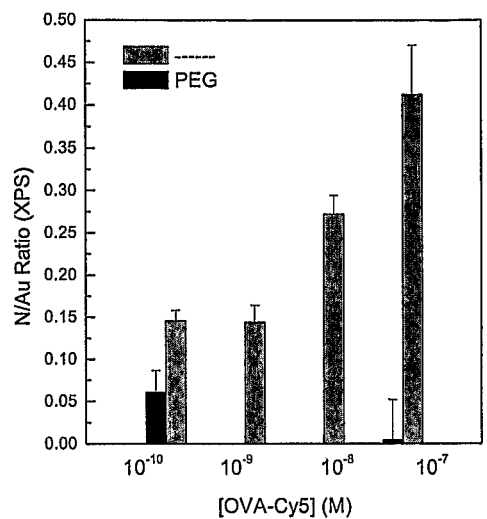
FIG. 16D is a graph of the results of the XPS spectra of FIG. 16A.
Figure 16E:
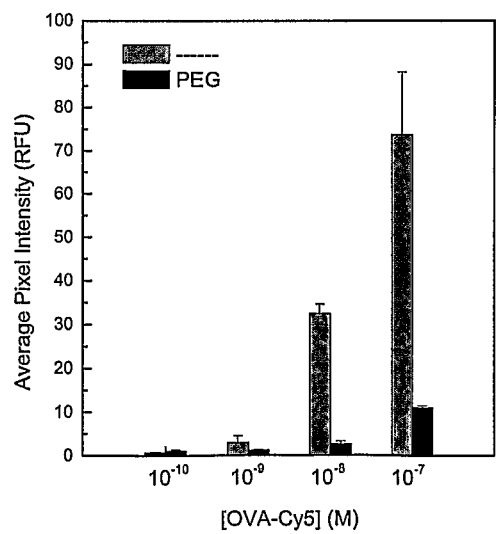
FIG. 16E is a graph of the pixel intensity for the fluorescent laser scanning analysis of FIGS. 16B and 16C.

Furthermore, a similar trend in non-specific binding was observed by both techniques as a function of protein concentration, and both techniques suggested a detection limit cut-off for non-specific adsorption at ~$10^{-9}$M, as shown in FIGS. 16D and 16E, respectively. Accordingly, this technique demonstrates the measuring of non-specific binding, and PEG coatings were shown to significantly reduce protein adsorption below the limit of detection of either instrument.

Experiment 11

Figure 17:
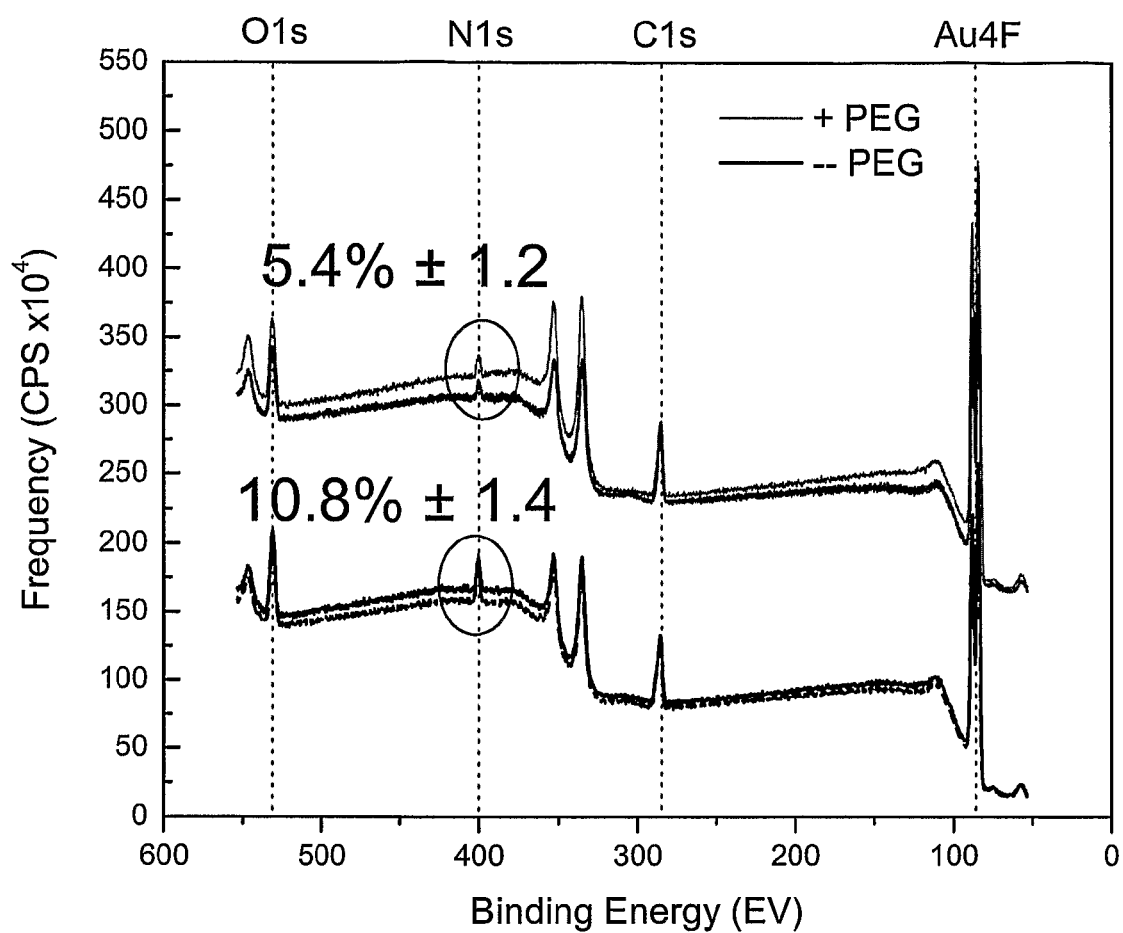
FIG. 17 is an example XPS spectra for coated and uncoated patches exposed to 10% mouse serum.

In FIG. 17 the results of XPS performed on PEG and non-PEG coated patches exposed to serum are shown. In this example, it is highlighted that PEG-patches reduced serum adsorption to patches by ~50%. This demonstrates that the use of PEG coating can be used to reduce non-specific absorption of serum, which is useful in identifying specific biological markers.

It will be appreciated that the use of appropriate polymer properties, such as molecular weight, degree of crosslinking, terminal group chemistry, monomer chemistry, polymerization/attachment conditions, or the like, can be used to reduce serum (and also patch-extracted fluid) protein adsorption by a greater degree.

Experiment 12

An example of the specific detection of antibodies raised in response to FluVax vaccination using surface modified patches will now be described.

In this example, in order to test the effect of PEG-patches on specific detection of biomarkers, a FluVax antigen or ovalbumin protein is further attached to the terminal carboxylic acid groups via standard EDC chemistry. After passivating an ELISA plate with bovine serum albumin in PBS (in order to minimize non-specific binding of serum to plate walls), patches (either uncoated, PEG coated, PEG-ovalbumin or PEG-FluVax) were add to each well (triplicate patches, 1 per well) and serum from naïve mice or mice immunized against FluVax was added (all mice C57 Black).

After washing away unbound material, a secondary antibody specific to IgG (goat-anti-mouse-IgG) and containing a Cy5 fluorophore was added (1:600 dilution) to bind any antibodies still coated to the patch in each particular well. Following a final wash step, the patches were scanned with a 647 nm laser and the Cy5 signal from the secondary antibody was recorded in the form of fluorescence micrographs.

Figure 18A:
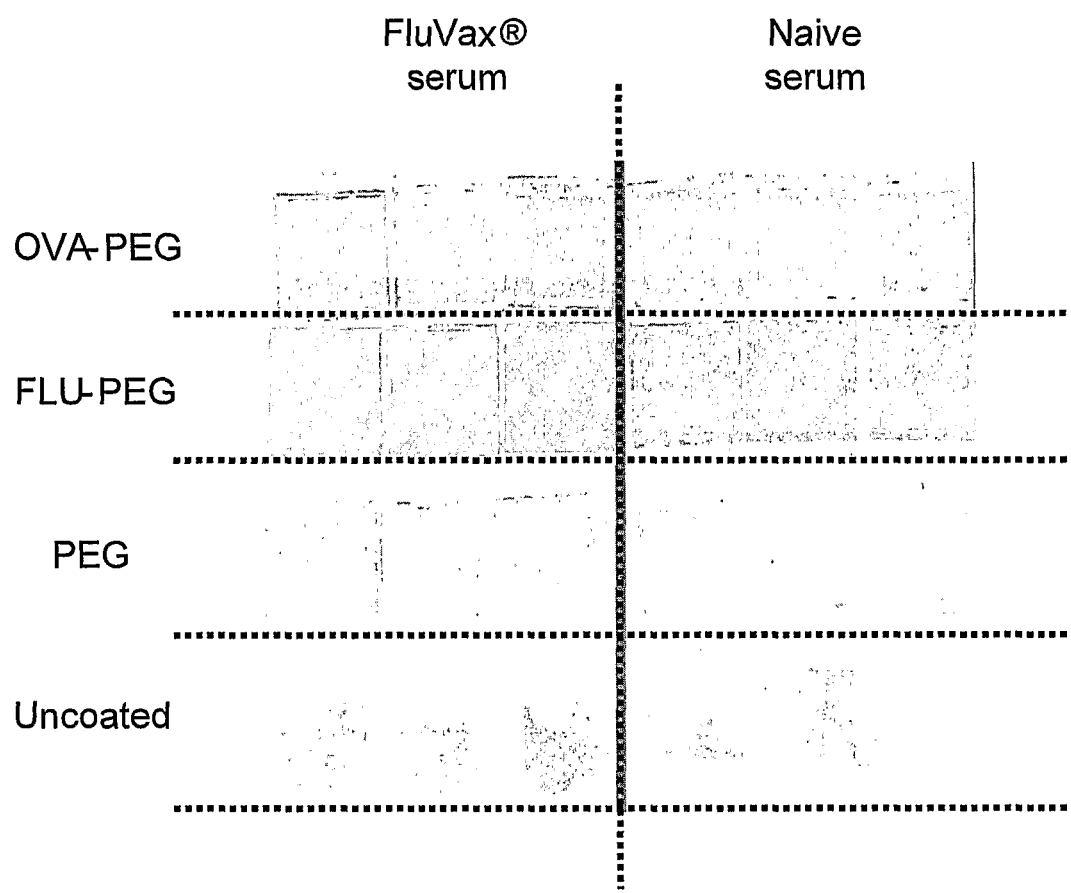
FIG. 18A is an example of fluorescence micrograph images for selectively coated patches with FluVax and Niave serum.
Figure 18B:
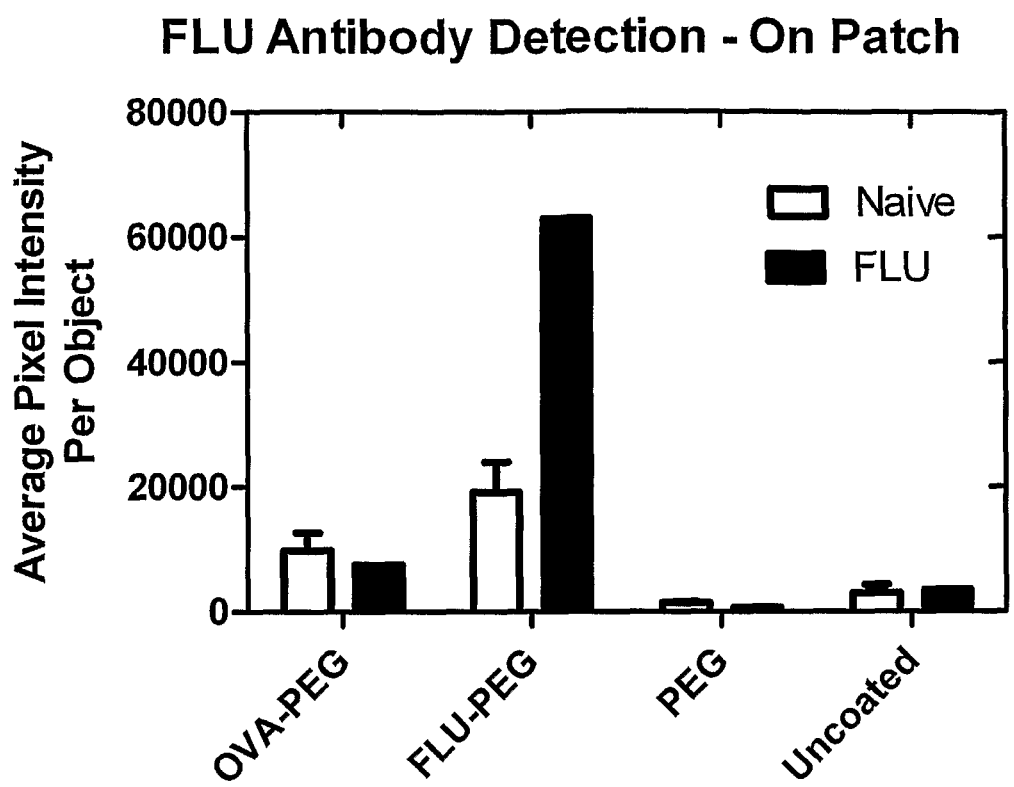
FIG. 18B is a graph of the average fluorescence intensity per patch for the patches of FIG. 18A; and, FIG. 19 is a graph of an example of the Cy5 fluorescence intensity for patches applied to immunised and naive mice.

Examples of the fluorescence micrographs for FluVax and Niave serum are shown in FIG. 18A (negative image shown for clarity), with the resulting fluorescence intensity being used to provide a column chart comparing the average intensity per patch, as shown in FIG. 18B.

It can be seen from the images/graphs that the PEG-FluVax patches were able to extract a significant amount of antibodies from the serum in comparison to any other patches, or the naïve serum control. Furthermore, PEG patches yielded the lowest binding of serum material of any patches, confirming the significant reduction of non-specific binding with respect to uncoated controls. Thus, the use of the PEG-FluVax coating, allows for the specific targeting of Flu-Vax antibodies, thereby highlighting the ability to produce a patch capable of discriminating specific analytes.

Experiment 12

A further example of the specific detection of antibodies raised in response to FluVax vaccination using surface modified patches applied to mouse skin will now be described.

Figure 19:
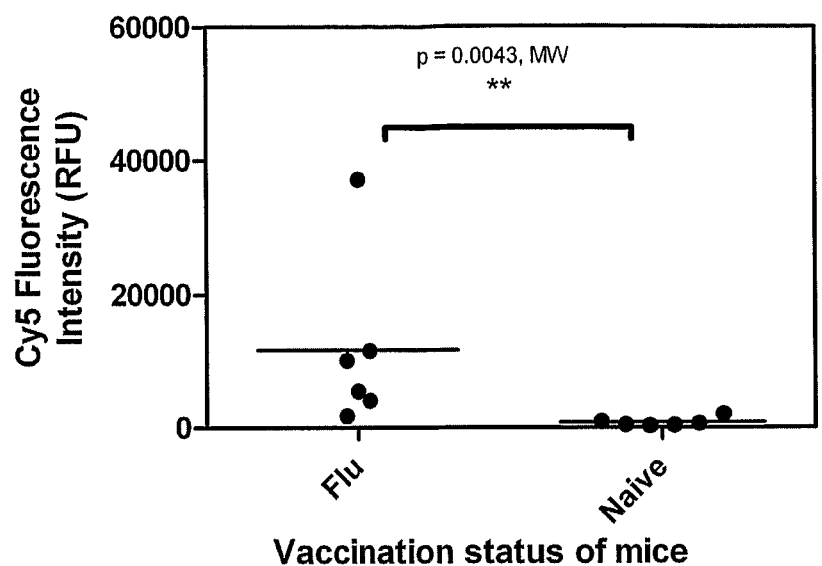

In this experiment, the PEG-FluVax patches described in experiment 11 above were applied to the ears of FluVax-immunised and naïve mice. The patches were then rinsed thoroughly and incubated with the same Cy5-labelled secondary antibody specific to IgG (goat-anti-mouse-IgG, 1:600 dilution). The results of analysis by laser scanning as described above are shown in FIG. 19. In the results, the Mann-Whitney U-test revealed a significant difference in Cy5 intensities between Fluvax-immunised mice and naïve controls, thereby highlighting the ability of the patch to successfully extract Flu-Vax antibodies from an immunised test subject.

Accordingly, the above described patch 100 allows analytes to be detected in specific tissue sites in the skin. In one example, this is achieved using coated projections allowing the analytes be to be either extracted for analysis in vitro. In this example, after analyte capture, the device can be removed from the skin and inserted into a vessel which can reveal the identity of the captured analyte via specific reaction with a reagent such as a fluoro-labelled protein/antibody/nucleic acid in a "sandwich assay" format.

Alternatively, the projections 110 can be coated with a reagent, allowing analytes to react with the reagent in vivo, such that the results of the reaction can be determined when the projections are removed from the subject.

The coatings can be specifically designed to capture analytes with extremely high specificity. Such specificity allows specific analytes of interest to be detected without the need for purification or complex chemical analysis.

The length of the projections can be controlled during manufacture to enable targeting of specific layers in the target tissue. In one example, this is performed to target analytes in the epidermal and/or dermal ISF, although analytes in capillary blood can also be targeted.

Specific probes can be localized to individual projections or areas of projections, so that multiple targets can be analysed in a single assay simply by their location in a 2-dimensional array. This could facilitate the analysis of disease-specific analyte panels to increase the sensitivity/specificity of the diagnostic results.

The projection patches can therefore provide a sampling device which overcomes the need for traditional blood or ISF samples to be taken for diagnostic purposes representing an opportunity for the GP to diagnose and avoid time and processing costs at centralized testing facilities. It may also open new markets since diagnostic equipment and blood sampling expertise is not needed e.g. in developing countries and 'in-field' military applications.

This allows patches to be used as a non-invasive, pain-free sample extraction platform instead of the current gold standard—microdialysis. The type of material isolated by the patch may be controlled by the length of the projections, such that ISF can be targeted specifically. This embodiment does not include a specific analysis type; a number of established techniques can be used for fluid analysis including, but not limited to, mass spectrometry, microarrays, DNA/protein sequencing, HPLC, ELISA, Western Blots and other gel methods, etc.

Using affinity surface coatings on each projection allow a reduction of non-specific adsorption of ISF components whilst facilitating specific extraction of the molecular targets of interest.

The patch can be used as the substrate for a direct assay to identify the target without the need for target labelling. For example the patch, once removed from the skin, could be used as the substrate for an ELISA reaction or for an embodiment based on protein detection.

By arranging the projections in a two-dimensional format, multiple probes can be attached to the same patch, with the results from the sandwich assay decoded based on the 2-D array position of the individual projections. This essentially allows array-style processing without the need for sample extraction, purification, labelling, etc.

As used herein, the term "analyte" refers to naturally occurring and/or synthetic compounds, which are a marker of a condition (e.g., drug abuse), disease state (e.g., infectious diseases), disorder (e.g., neurological disorders), or a normal or pathologic process that occurs in a patient (e.g., drug metabolism). The term "analyte" can refer to any substance, including chemical and/or biological agents that can be measured in an analytical procedure, including nucleic acids, proteins, illicit drugs, explosives, toxins, pharmaceuticals, carcinogens, poisons, allergens, and infectious agents, which can be measured in an analytical procedure.

Analytes may be a member of a specific binding pair (sbp), with a binding partner being other member of the specific binding pair. The analyte or the binding partner may be a ligand, which is monovalent (monoepitopic) or polyvalent (polyepitopic), usually antigenic or haptenic, and is a single compound or plurality of compounds that share at least one common epitopic or determinant site. The analyte can be a part of a cell such as a bacterium or a cell bearing a blood group antigen such as A, B, D, etc., or an HLA antigen or the analyte may be a microorganism, e.g., bacterium, fungus, protozoan, or virus. In certain circumstances the analyte may be a reference compound, a control compound, a calibrator, and the like.

The monoepitopic ligand analytes will generally be from about 100 to about 2,000 molecular weight, more usually, from about 125 to about 1,000 molecular weight. Non-limiting examples of monoepitopic analytes include drugs, e.g., drugs of abuse and therapeutic drugs, metabolites, pesticides, pollutants, nucleosides, and the like. Included among drugs of interest are the alkaloids, steroids, lactams, aminoalkylbenzenes, benzheterocyclics, purines, drugs derived from marijuana, hormones, vitamins, prostaglandins, tricyclic antidepressants, anti-neoplastics, aminoglycosides, antibiotics, nucleosides and nucleotides, miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives, and so forth.

Metabolites related to diseased states include spermine, galactose, phenylpyruvic acid, and porphyrin Type 1 and so forth.

Among pesticides of interest are polyhalogenated biphenyls, phosphate esters, thiophosphates, carbamates, polyhalogenated sulfenamides, their metabolites and derivatives.

The polyvalent ligand analytes will normally be poly (amino acids), e.g., polypeptides and proteins, polysaccharides, mucopolysaccharides, nucleic acids, and combinations thereof. Such combinations include components of bacteria, viruses, chromosomes, genes, mitochondria, nuclei, cell membranes and the like.

A polynucleotide or nucleic acid is a compound or composition that is a polymeric nucleotide or nucleic acid polymer, which may include modified nucleotides.

For the most part, the polyepitopic ligand analytes to which the techniques can be applied have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins is contemplated in the above examples, including proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Illustrative examples of this type include protamines, histones, albumins, globulins, scleroproteins, phosphoproteins, mucoproteins, chromoproteins, lipoproteins, nucleoproteins, glycoproteins, T-cell receptors, proteoglycans, human leukocyte antigen (HLA), unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. In other embodiments, the polymeric materials of interest are mucopolysaccharides and polysaccharides.

Other illustrative examples of polypeptide analytes include insulin, proinsulin, follicle stimulating hormone, insulin like growthfactor-1, insulin like growth factor-2, platelet derived growth factor, epidermal growth factor, fibroblast growth factors, nerve growth factor, colony stimulating factors, transforming growth factors, tumor necrosis factor, calcitonin, parathyroid hormone, growth hormone, bone morphogenic protein, erythropoietin, hemopoietic growth factors, luteinizing hormone, glucagon, glucagon like peptide-1, anti-angiogenic proteins, clotting factors, anti-clotting factors, atrial natriuretic factor, plasminogen activators, bombesin, thrombin, enkephalinase, vascular endothelial growth factor, interleukins, viral antigens, non-viral antigens, transport proteins, and antibodies.

In still other embodiments, the polypeptide analyte is a receptor, illustrative examples of which include Fc receptor, heparin sulfate receptor, vitronectin receptor, Vcam-1 receptor, hemaglutinin receptor, Pvr receptor, Icam-1 receptor, decay-accelerating protein (CD55) receptor, Car (coxsackievirus-adenovirus) receptor, integrin receptor, sialic acid receptor, HAVCr-1 receptor, low-density lipoprotein receptor, BGP (biliary glycoprotein) receptor, aminopeptidase N receptor, MHC class-1 receptor, laminin receptor, nicotinic acetylcholine receptor, CD56 receptor, nerve growth factor receptor, CD46 receptor, asialoglycoprotein receptor Gp-2, alpha-dystroglycan receptor, galactosylceramide receptor, Cxcr4 receptor, Glvr1 receptor, Ram-1 receptor, Cat receptor, Tva receptor, BLVRcp1 receptor, MHC class-2 receptor, toll-like receptors (such as TLR-1 to -6) and complement receptors.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

In still other embodiments, polypeptide analytes are selected from antigens including endogenous antigens produced by a host or exogenous antigens that are foreign to that host. The antigens may be in the form of soluble peptides or polypeptides or polynucleotides from which an expression product (e.g., protein or RNA) is producible. Suitable endogenous antigens include, but are not restricted to, cancer or tumor antigens. Non-limiting examples of cancer or tumor antigens include antigens from a cancer or tumor selected from ABL1 proto-oncogene, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, dermatofibrosarcoma protuberans, desmoplastic small round cell tumor, ductal carcinoma, endocrine cancers, endometrial cancer, ependymoma, oesophageal cancer, Ewing's Sarcoma, Extra-Hepatic Bile Duct Cancer, Eye Cancer, Eye: Melanoma, Retinoblastoma, Fallopian Tube cancer, Fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynecological cancers, haematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's cell histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid tumor of kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer (NSCLC), ocular cancers, esophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal tumours, pituitary cancer, polycythemia vera, prostate cancer, rare cancers and associated disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis–/– ureter), trophoblastic cancer, urethral cancer, urinary system cancer, uroplakins, uterine sarcoma, uterus cancer, vaginal cancer, vulva cancer, Waldenstrom's macroglobulinemia, Wilms' tumor. In certain embodiments, the cancer or tumor relates to melanoma. Illustrative examples of melanoma-related antigens include melanocyte differentiation antigen (e.g., gp100, MART, Melan-A/MART-1, TRP-1, Tyros, TRP2, MC1R, MUC1F, MUC1R or a combination thereof) and melanoma-specific antigens (e.g., BAGE, GAGE-1, gp100In4, MAGE-1 (e.g., GenBank Accession No. X54156 and AA494311), MAGE-3, MAGE4, PRAME, TRP21N2, NYNSO1a, NYNSO1b, LAGE1, p97 melanoma antigen (e.g., GenBank Accession No. M12154) p5 protein, gp75, oncofetal antigen, GM2 and GD2 gangliosides, cdc27, p21ras, gp100$^{Pmel117}$ or a combination thereof. Other tumour-specific antigens include, but are not limited to: etv6, aml1, cyclophilin b (acute lymphoblastic leukemia); Ig-idiotype (B cell lymphoma); E-cadherin, α-catenin, β-catenin, γ-catenin, p120ctn (glioma); p21ras (bladder cancer); p21ras (biliary cancer); MUC family, HER2/neu, c-erbB-2 (breast cancer); p53, p21ras (cervical carcinoma); p21ras, HER2/neu, c-erbB-2, MUC family, Cripto-1protein, Pim-1 protein (colon carcinoma); Colorectal associated antigen (CRC)-CO17-1A/GA733, APC (colorectal cancer); carcinoembryonic antigen (CEA) (colorectal cancer; choriocarcinoma); cyclophilin b (epithelial cell cancer); HER2/neu, c-erbB-2, ga733 glycoprotein (gastric cancer); α-fetoprotein (hepatocellular cancer); Imp-1, EBNA-1 (Hodgkin's lymphoma); CEA, MAGE-3, NY-ESO-1 (lung cancer); cyclophilin b (lymphoid cell-derived leukemia); MUC family, p21ras (myeloma); HER2/neu, c-erbB-2 (non-small cell lung carcinoma); Imp-1, EBNA-1 (nasopharyngeal cancer); MUC family, HER2/neu, c-erbB-2, MAGE-A4, NY-ESO-1 (ovarian cancer); Prostate Specific Antigen (PSA) and its antigenic epitopes PSA-1, PSA-2, and PSA-3, PSMA, HER2/neu, c-erbB-2, ga733 glycoprotein (prostate cancer); HER2/neu, c-erbB-2 (renal cancer); viral products such as human papillomavirus proteins (squamous cell cancers of the cervix and esophagus); NY-ESO-1 (testicular cancer); and HTLV-1 epitopes (T cell leukemia).

Foreign antigens are suitably selected from transplantation antigens, allergens as well as antigens from pathogenic organisms. Transplantation antigens can be derived from donor cells or tissues from e.g., heart, lung, liver, pancreas, kidney, neural graft components, or from the donor antigen-presenting cells bearing MHC loaded with self antigen in the absence of exogenous antigen.

Non-limiting examples of allergens include Fel d 1 (i.e., the feline skin and salivary gland allergen of the domestic cat Felis domesticus, the amino acid sequence of which is disclosed International Publication WO 91/06571), Der p I, Der p II, Der fI or Der fII (i.e., the major protein allergens from the house dust mite dermatophagoides, the amino acid sequence of which is disclosed in International Publication WO 94/24281). Other allergens may be derived, for example from the following: grass, tree and weed (including ragweed) pollens; fungi and molds; foods such as fish, shellfish, crab, lobster, peanuts, nuts, wheat gluten, eggs and milk; stinging insects such as bee, wasp, and hornet and the chirnomidae (non-biting midges); other insects such as the housefly, fruitfly, sheep blow fly, screw worm fly, grain weevil, silkworm, honeybee, non-biting midge larvae, bee moth larvae, mealworm, cockroach and larvae of Tenibrio molitor beetle; spiders and mites, including the house dust mite; allergens found in the dander, urine, saliva, blood or other bodily fluid of mammals such as cat, dog, cow, pig, sheep, horse, rabbit, rat, guinea pig, mouse and gerbil; airborne particulates in general; latex; and protein detergent additives.

In some embodiments, the polypeptide analyte is an antigen relating to a pathogenic organism. Exemplary pathogenic organisms include, but are not limited to, viruses, bacteria, fungi parasites, algae and protozoa and amoebae. Illustrative viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, influenza virus, Japanese encephalitis (e.g., GenBank Accession No. E07883), dengue (e.g., GenBank Accession No. M24444), hantavirus, Sendai virus, respiratory syncytial virus, othromyxoviruses, vesicular stomatitis virus, visna virus, cytomegalovirus and human immunodeficiency virus (HIV) (e.g., GenBank Accession No. U18552). Any suitable antigen derived from such viruses are useful in the practice of the above described processes. For example, illustrative retroviral antigens derived from HIV include, but are not limited to, antigens such as gene products of the gag, pol, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neurarninidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of cytomegaloviral antigens include, but are not limited to, antigens such as envelope glycoprotein B and other cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, 80% E, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers, See Fundamental Virology, Second Edition, eds. Fields, B. N. and Knipe, D. M., 1991, Raven Press, New York, for additional examples of viral antigens.

In other embodiments, the polypeptide analyte is selected from fungal antigens. Illustrative examples of fungi include Acremonium spp., Aspergillus spp., Basidiobolus spp., Bipolaris spp., Blastomyces dermatidis, Candida spp., Cladophialophora carrionii, Coccoidiodes immitis, Conidiobolus spp., Cryptococcus spp., Curvularia spp., Epidermophyton spp., Exophiala jeanselmei, Exserohilum spp., Fonsecaea compacta, Fonsecaea pedrosoi, Fusarium oxysporum, Fusarium solani, Geotrichum candidum, Histoplasma capsulatum var. capsulatum, Histoplasma capsulatum var. duboisii, Hortaea werneckii, Lacazia loboi, Lasiodiplodia theobromae, Leptosphaeria senegalensis, Madurella grisea, Madurella mycetomatis, Malassezia furfur, Microsporum spp., Neotestudina rosatii, Onychocola canadensis, Paracoccidioides brasiliensis, Phialophora verrucosa, Piedraia hortae, Piedra iahortae, Pityriasis versicolor, Pseudallesheria boydii, Pyrenochaeta romeroi, Rhizopus arrhizus, Scopulariopsis brevicaulis, Scytalidium dimidiatum, Sporothrix schenckii, Trichophyton spp., Trichosporon spp., Zygomcete fungi, Absidia corymbifera, Rhizomucor pusillus and Rhizopus arrhizus. Thus, representative fungal antigens that can be used in the compositions and methods described above include, but are not limited to, candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

In still other embodiments, the polypeptide analyte is selected from bacterial antigens. Illustrative examples of bacteria include bacteria that are responsible for diseases including, but not restricted to, diphtheria (e.g., Corynebacterium diphtheria), pertussis (e.g., Bordetella pertussis, GenBank Accession No. M35274), tetanus (e.g., Clostridium tetani, GenBank Accession No. M64353), tuberculosis (e.g., Mycobacterium tuberculosis), bacterial pneumonias (e.g., Haemophilus influenzae.), cholera (e.g., Vibrio cholerae), anthrax (e.g., Bacillus anthracis), typhoid, plague, shigellosis (e.g., Shigella dysenteriae), botulism (e.g., Clostridium botulinum), salmonellosis (e.g., GenBank Accession No. L03833), peptic ulcers (e.g., Helicobacter pylori), Legionnaire's Disease, Lyme disease (e.g., GenBank Accession No. U59487), Other pathogenic bacteria include Escherichia coli, Clostridium perfringens, Pseudomonas aeruginosa, Staphylococcus aureus and Streptococcus pyogenes. Thus, bacterial antigens which can be used in the compositions and methods described above include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; Mycobacterium tuberculosis bacterial antigens such as mycolic acid, heat shock protein 65 (HSP65), the 30 kDa major secreted protein, antigen 85A and other mycobacterial antigen components; Helicobacter pylori bacterial antigen components, pneumococcal bacterial antigens such as pneumolysin, pneumococcal capsular polysaccharides and other pnermiococcal bacterial antigen components; Haemophilus influenza bacterial antigens such as capsular polysaccharides and other Haemophilus influenza bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

In still other embodiments, the polypeptide analyte is selected from protozoal antigens. Illustrative examples of protozoa include protozoa that are responsible for diseases including, but not limited to, malaria (e.g., GenBank Accession No. X53832), hookworm, onchocerciasis (e.g., GenBank Accession No. M27807), schistosomiasis (e.g., GenBank Accession No. LOS198), toxoplasmosis, trypanosomiasis, leishmaniasis, giardiasis (GenBank Accession No. M33641), amoebiasis, filariasis (e.g., GenBank Accession No. J03266), borreliosis, and trichinosis. Thus, protozoal antigens which can be used in the compositions and methods described above include, but are not limited to: plasmodium falciparum antigens such as merozoite surface antigens, sporozoite surface antigens, circumsporozoite antigens, gametocyte/gamete surface antigens, blood-stage antigen pf 155/RESA and other plasmodial antigen components; toxoplasma antigens such as SAG-1, p30 and other toxoplasmal antigen components; schistosomae antigens such as glutathione-S-transferase, paramyosin, and other schistosomal antigen components; leishmania major and other leishmaniae antigens such as gp63, lipophosphoglycan and its associated protein and other leishmanial antigen components; and trypanosoma cruzi antigens such as the 75-77 kDa antigen, the 56 kDa antigen and other trypanosomal antigen components.

The above described processes also contemplate toxin components as analytes. Illustrative examples of toxins include, but are not restricted to, staphylococcal enterotoxins, toxic shock syndrome toxin; retroviral antigens (e.g., antigens derived from HIV), streptococcal antigens, staphyloccal enterotoxin-A (SEA), staphylococcal enterotoxin-B (SEB), staphylococcal enterotoxin$_{1-3}$ (SE$_{1-3}$), staphylococcal enterotoxin-D (SED), staphylococcal enterotoxin-E (SEE) as well as toxins derived from mycoplasma, mycobacterium, and herpes viruses.

The term analyte further includes nucleic acid analytes, illustrative examples of which include DNA, RNA, sense oligonucleotides, antisense oligonucleotides, ribozymes, small interfering oligonucleotides (siRNAs), micro RNAs (miRNAs), repeat associated RNAs (rasiRNA), effector RNAs (eRNAs), and any other oligonucleotides known in the art, which inhibit transcription and/or translation of a mutated or other detrimental protein. In illustrative examples of this type, the nucleic acid is in the form of an expression vector from which a polynucleotide of interest is expressible. The polynucleotide of interest may encode a polypeptide or an effector nucleic acid molecule such as sense or antisense oligonucleotides, siRNAs, miRNAs and eRNAs. The term analyte also includes receptors that are polynucleotide binding agents, such as, for example, restriction enzymes, activators, repressors, nucleases, polymerases, histones, repair enzymes, chemotherapeutic agents, and the like.

Also included within the term analyte are polysaccharides or carbohydrates, lipids, fatty acids and the like.

The analyte may be a biomarker, which is a biochemical feature or facet that can be used to measure the progress of a disease or illness or the effects of treatment of a disease or illness. The biomarker may be, for example, a virus, a bacterium, a cancer antigen, a heart disease indicator, a stroke indicator, an Alzheimer's disease indicator, and the like.

The analytes may be molecules found directly in a sample such as biological tissue, including body fluids, from a host. The sample can be examined directly or may be pretreated to render the analytes more readily detectable. Furthermore, the analytes of interest may be determined by detecting agents probative of the analytes of interest such as a specific binding pair member complementary to the analyte of interest, whose presence will be detected only when a particular analyte of interest is present in a sample. Thus, the agent probative of the analyte becomes the analyte that is detected in an assay.

The above described patches may also be used to test other forms of subjects, such as food stuffs, or the like. In this example, the patch could be used to test for the presence of unwanted contaminants, such as pathogens, such as bacteria, exotoxins, mycotoxins, viruses, parasites, or the like, as well as natural toxins. Additionally contaminants could include agrochemicals, environmental contaminants, pesticides, carcinogens, or the like. bacteria, or the like.

Typical bacteria include Campylobacter jejuni which can lead to secondary Guillain-Barré syndrome and periodontitis, Clostridium perfringens, Salmonella spp., Escherichia coli O157:H7 enterohemorrhagic (EHEC) which causes hemolytic-uremic syndrome, Bacillus cereus, Escherichia coli, other virulence properties, such as enteroinvasive (EIEC), enteropathogenic (EPEC), enterotoxigenic (ETEC), enteroaggregative (EAEC or EAgEC), Salmonella Listeria monocytogenes Shigella spp., Staphylococcus aureus, Streptococcus, Vibrio cholerae, including O1 and non-O1, Vibrio parahaemolyticus, Vibrio vulnificus, Yersinia enterocolitica and Yersinia pseudotuberculosis. Other bacterial agents include Brucella spp., Corynebacterium ulcerans, Coxiella burnetii or Q fever, and Plesiomonas shigelloides.

Exotoxinds can include Clostridium botulinum, Clostridium perfringens, Staphylococcus aureus, Bacillus cereus, and Pseudoalteromonas tetraodonis.

Common foodborne Mycotoxins include Aflatoxins, Altertoxins including Alternariol (AOH), Alternariol methyl ether (AME), Altenuene (ALT), Altertoxin-1 (ATX-1), Tenuazonic acid (TeA) and Radicinin (RAD), Citrinin, Citreoviridin, Cyclopiazonic acid, Cytochalasins, Ergot alkaloids/Ergopeptine alkaloids, Ergotamine, Fumonisins, Fusaric acid, Fusarochromanone, Kojic acid, Lolitrem alkaloids, Moniliformin, 3-Nitropropionic acid, Nivalenol, Ochratoxins, Oosporeine, Patulin, Phomopsins, Sporidesmin A, Sterigmatocystin, Tremorgenic mycotoxins, Zearalenone and, Zearalenols.

Typically viruses include Rotavirus Enterovirus, Hepatitis E, Norovirus, Rotavirus. Parasites can includes Platyhelminthes, such as Diphyllobothrium sp., Nanophyetus sp., Taenia saginata, Taenia solium, Fasciola hepatica, Nematodes, such as Anisakis sp., Ascaris lumbricoides, Eustrongylides sp., Trichinella spiralis, Trichuris trichiura and Protozoa, such as Acanthamoeba and other free-living amoebae, Cryptosporidium parvum, Cyclospora cayetanensis, Entamoeba histolytica, Giardia lamblia., Sarcocystis hominis, Sarcocystis suihominis, Toxoplasma gondii.

Natural toxins can include Alkaloids, Ciguatera poisoning, Grayanotoxin (honey intoxication), Mushroom toxins, Phytohaemagglutinin, Pyrrolizidine alkaloids, Shellfish toxin, Scombrotoxin, Tetrodotoxin.

Agrochemicals can include pesticides, such as insecticides, herbicides, rodenticides, plant growth regulators, veterinary drugs such as nitrofuran, fluoroquinolones, malachite green, chloramphenicol, and bovine somatotropin (rBST).

Environmental contaminants can include radionuclides (137Caesium, 90Strontium), polycyclic aromatic hydrocarbons (PAH), arsenic, mercury, cadmium, nitrates, perchlorates, Polychlorinated biphenyls (PCB), dioxins, and polybrominated diphenyl ethers (PBDE), antimony, tin, lead, perfluorooctanoic acid (PFOA), semicarbazide, benzophenone, isopropylthioxanthone (ITX), bisphenol A, copper, or other metal chips, lubricants, cleaning and sanitizing agents.

Accordingly, through suitable configuration, this can allow the patches to be used to test food stuffs prior to consumption. In one example, the patch is inserted directly into the food product, allowing material to be extracted and contaminants identified. By suitable configuration of the patches, this could be achieved by performed prior to removal of the foodstuff from any packaging, thereby reducing the likelihood of exposure of the individual performing the testing to the contaminant.

In one example, by inclusion of suitable reagents on the patch, or in a separate reservoir or the like, a simple colour change could be induced upon presence of one or more selected contaminants, thereby indicating that the food stuff is unsuitable for human consumption. This provides a simple technique for allowing individual to test foodstuffs prior to consumption.

Accordingly, it will be appreciated that the term subject can include living subjects, such as humans, animals, or plants, as well as nonliving materials, such as foodstuffs, packaging; or the like.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. An apparatus for use in detecting analytes in a subject, wherein the apparatus includes:
   a) a number of projections provided on a patch, wherein the projections include a support section and a targeting section, such that applying the patch to the subject causes at least some of the projections to be inserted into the subject and target one or more analytes;
b) a coating applied to at least some of the projections, wherein the coating includes at least a first probe for selectively targeting first analytes of interest and a second probe, different from the first probe, for selectively targeting second analytes of interest; and,
c) a reagent for detecting the presence or absence of analytes.

2. The apparatus according to claim 1, wherein the coating includes a reagent for reacting with analytes in the subject.

3. The apparatus according to claim 1, wherein the coating is for extracting analytes when the projections are removed from the subject.

4. The apparatus according to claim 3, wherein the coating includes a binding agent for binding with analytes of interest.

5. The apparatus according to claim 1, wherein the coating includes a material to repel at least some analytes from the projections.

6. The apparatus according to claim 5, wherein the material includes a polymer.

7. The apparatus according to claim 1, wherein the coating includes:
a) a first coating layer for repelling analytes; and,
b) a second coating layer including at least one of:
  i) a binding agent for binding with analytes of interest; and,
  ii) a reagent for reacting with analytes of interest.

8. The apparatus according to claim 7, wherein, for projections coated with the first coating, the first coating is applied to substantially all of the projection.

9. The apparatus according to claim 7, wherein, for projections coated with the second coating, the second coating is applied to a tip of the projection.

10. The apparatus according to claim 1, wherein the apparatus includes:
a) at least first projections for targeting first analytes; and,
b) at least second projections for targeting second analytes.

11. The apparatus according to claim 10, wherein:
a) the first projections are coated with a first binding agent; and,
b) the second projections are coated with a second binding agent.

12. The apparatus according to claim 10, wherein:
a) the first projections have a first geometry; and,
b) the second projections have a second geometry.

13. The apparatus according to claim 1, wherein the projections are for absorbing analytes.

14. The apparatus according to claim 13, wherein the projections are for selectively absorbing analytes of interest.

15. The apparatus according to claim 1, wherein the projections include one or more pores, the pores being adapted to receive analytes.

16. The apparatus according to claim 1, wherein the pores have a size for targeting analytes of interest.

17. The apparatus according to claim 1, wherein the projections include a binding agent distributed therein, the binding agent being for binding with analytes of interest.

18. The apparatus according to claim 1, wherein the projections are at least one of:
a) polymer projections;
b) silicon projections; and,
c) organosilicate projections.

19. The apparatus according to claim 1, wherein the apparatus includes a housing defining at least one well, wherein in use the at least one well contains a solution including a reagent, such that in use, at least some of the projections can be inserted into the well, thereby allowing the analytes to react with the reagent.

20. The apparatus according to claim 19, wherein the housing defines a plurality of wells for receiving respective projections.

21. The apparatus according to claim 20, wherein each well contains a solution including a respective reagent, such that in use, at least some of the projections can be inserted into each well, thereby allowing analytes to react with a number of different reagents.

22. The apparatus according to claim 21, wherein the patch includes respective areas of projections, each area of projections being for extracting a respective analyte, and wherein the areas are arranged such that each area of projections is inserted into a respective well, thereby allowing different analytes to react with respective reagents.

23. The apparatus according to claim 22, wherein the projections are configured to target analytes in at least one of:
a) an epidermal layer in the subject;
b) a dermal layer in the subject;
c) a capillary layer in the subject;
d) an epithelial layer; and,
e) any accessible surface layer in the subject.

24. The apparatus according to claim 1, wherein the length of the projections prevents the projections entering the dermis.

25. The apparatus according to claim 1, wherein the targeting section has a diameter of less than at least one of:
a) 1 µm; and,
b) 0.5 µm.

26. The apparatus according to claim 1, wherein a length for the targeting section is at least:
a) less than 0.5 µm; and,
b) less than 1.0 µm; and,
c) less than 2.0 µm.

27. The apparatus according to claim 1, wherein a length for the support section is <200 µm.

28. The apparatus according to claim 1, wherein the projections are solid.

29. The apparatus according to claim 1, wherein the projections are non-porous and non-hollow.

30. The apparatus according to claim 1, wherein the reagent reacts with analytes to generate a visible indication.

31. The apparatus according to claim 1, wherein the analytes include at least one of:
a) epigenetic markers;
b) short RNA species;
c) nucleic acids or proteins;
d) antigens, allergens, or adjuvants;
e) parasites, bacteria, viruses, or virus-like particles;
f) immunoglobulins; and,
g) cells.

32. The apparatus according to claim 1, wherein the apparatus includes:
a) a flexible substrate; and,
b) a number of patches, each patch including a number of projections for penetrating a body surface, the number of patches being mounted to a flexible backing.

33. The apparatus according to claim 1, wherein the detection of analytes is used in determining the presence, absence or concentration of one or more analytes in the subject.

34. A method for use in detecting analytes in a subject, wherein the method includes:
a) applying a patch to the subject such that a number of projections arranged on the patch are inserted into the subject and target one or more analytes, wherein the projections include a support section and a targeting section, wherein a coating is applied to at least some of the projections, and wherein the coating includes at least a first probe for selectively targeting first analytes of interest and a second probe, different from the first probe, for selectively targeting second analytes of interest;

b) removing the projections from the subject; and, c) using a reagent to determine the presence or absence of analytes.

35. The method according to claim 34, wherein the method includes:

a) removing the projections from the subject; and, b) exposing the analytes to the reagent.

36. The apparatus according to claim 1, wherein the first probe is for targeting first biological markers and the second probe is for targeting second biological markers.

37. The apparatus according to claim 1, wherein the apparatus includes:

a) first projections for targeting the first analytes of interest, wherein the first projections are coated with the first probe; and, b) second projections for targeting the second analytes of interest, wherein the second projections are coated with the second probe.

38. The apparatus according to claim 37, wherein the apparatus includes a housing defining first and second wells for receiving the first and second projections respectively, wherein in use each well contains a solution including a respective reagent, such that in use, at least some of the first projections can be inserted into the first well and at least some of the second projections can be inserted into the second well, thereby allowing the first and second analytes of interest to react with respective reagents.

39. A method of producing a patch for use in detecting analytes in a subject, wherein the method includes applying a coating to a number of projections provided on the patch, wherein the projections include a support section and a targeting section, the projections being arranged such that applying the patch to the subject causes at least some of the projections to be inserted into the subject and target one or more analytes, the coating including at least a first probe for selectively targeting first analytes of interest and a second probe, different from the first probe, for selectively targeting second analytes of interest and being for at least one of:

a) for reacting a reagent with analytes in the subject; and, b) extracting analytes when the projections are removed from the subject.

40. An apparatus for use in sampling analytes in a subject, wherein the apparatus includes:

a) a number of projections provided on a patch, wherein the projections include a support section and a targeting section, such that applying the patch to the subject causes at least some of the projections to be inserted into the subject; and, b) a coating applied to at least some of the projections, the coating including a binding agent for binding at least some analytes to the projections, thereby extracting analytes when the projections are removed from the subject, wherein the coating includes at least a first probe for selectively targeting first analytes of interest and a second probe, different from the first probe, for selectively targeting second analytes of interest.

41. An apparatus for use in detecting analytes in a subject, wherein the apparatus includes:

a) a number of projections provided on a patch, wherein the projections include a support section and a targeting section, such that applying the patch to the subject causes at least some of the projections to be inserted into the subject; and, b) a coating applied to at least some of the projections, the coating including:

i) at least a first probe for selectively targeting first analytes of interest and a second probe, different from the first probe, for selectively targeting second analytes of interest; and, ii) a reagent for reacting with analytes in the subject, thereby allowing the presence of analytes to be determined when the projections are removed from the subject.

42. A kit for use in detecting analytes in a subject, wherein the kit including:

a) a number of projections provided on a patch, wherein the projections include a support section and a targeting section, such that applying the patch to the subject causes at least some of the projections to be inserted into the subject and target one or more analytes;

b) a coating applied to at least some of the projections, wherein the coating includes at least a first probe for selectively targeting first analytes of interest and a second probe, different from the first probe, for selectively targeting second analytes of interest; and, c) a reagent for detecting the presence or absence of analytes.

* * * * *